(12) United States Patent
Muller

(10) Patent No.: US 6,214,614 B1
(45) Date of Patent: *Apr. 10, 2001

(54) CELL CYCLE REGULATED REPRESSOR AND DNA ELEMENT

(75) Inventor: Rolf Muller, Marburg (DE)

(73) Assignee: Aventis Pharma Deutschland GmbH (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/793,660

(22) PCT Filed: Aug. 23, 1995

(86) PCT No.: PCT/GB95/02000

§ 371 Date: Sep. 9, 1997

§ 102(e) Date: Sep. 9, 1997

(87) PCT Pub. No.: WO96/06943

PCT Pub. Date: Mar. 7, 1996

(30) Foreign Application Priority Data

Aug. 26, 1994 (GB) .................................... 9417366
Mar. 29, 1995 (GB) .................................... 9506466

(51) Int. Cl.[7] ........................... C12N 15/63; C07H 21/04

(52) U.S. Cl. ...................... 435/320.1; 536/24.1

(58) Field of Search ................. 435/320.1; 514/44; 536/23.1, 23.5, 24.1; 530/350

(56) References Cited

U.S. PATENT DOCUMENTS

| 5,830,880 | 11/1998 | Sedlacek et al. ................ 514/44 |
| 5,854,019 | 12/1998 | Sedlacek et al. ................ 435/69.1 |
| 5,885,833 | 3/1999 | Mueller et al. ................ 435/372 |
| 5,916,803 | 6/1999 | Sedlacek et al. ................ 435/320.1 |

OTHER PUBLICATIONS

Dalton (1992) Cell cycle regulation of the human cdc2 gene. EMBO j. 11:1797–1804, May 1992.*

Verma et al. (1997) Gene therapy–promises, problems and prospects. Nature 389:239–242, Sep. 1997.*

Lucibello, F.C., et al. *Periodic cdc25C transcription is mediated by a novel cell cycle–regulated repressor element (CDE)*. The EMBO Journal, vol. 14, 1995, 132–142.

Herber, B. et al., *Inducible regulatory elements in the human cyclin D1 promoter*. Oncogene, vol. 9, 1994, 1295–1304.

Nevins, J.R. *E2F: A Link Between the Rb Tumor Suppressor Protein and Viral Oncoproteins*. Science, vol. 258, 1992, 424–429.

Weitz, J. et al. *A Novel Nuclear Inhibitor I–92 Regulates DNA Binding Activity of Octamer Binding Protein p92 During the Cell Cycle*. Nucleic Acids Research, vol. 19, 1991, 5725–5730.

British Journal of Haematology, *Abstracts of papers presented at the First Meeting of the European Haematology Association*, Brussels Belgium, Jun. 2–5, 1994. vol. 87. Ehlert et al.

* cited by examiner

*Primary Examiner*—Robert A. Schwartzman
(74) *Attorney, Agent, or Firm*—Dike, Bronstein, Roberts & Cushman, LLP; David G. Conlin; Cara Z. Lowen

(57) ABSTRACT

The present invention relates to a cell cycle regulated repressor protein which binds to a DNA element present in the control sequences of the human cdc25C gene and other cell cycle regulated genes, as well as the use thereof in cell cycle regulated expression systems.

9 Claims, 16 Drawing Sheets

Figure 1A:
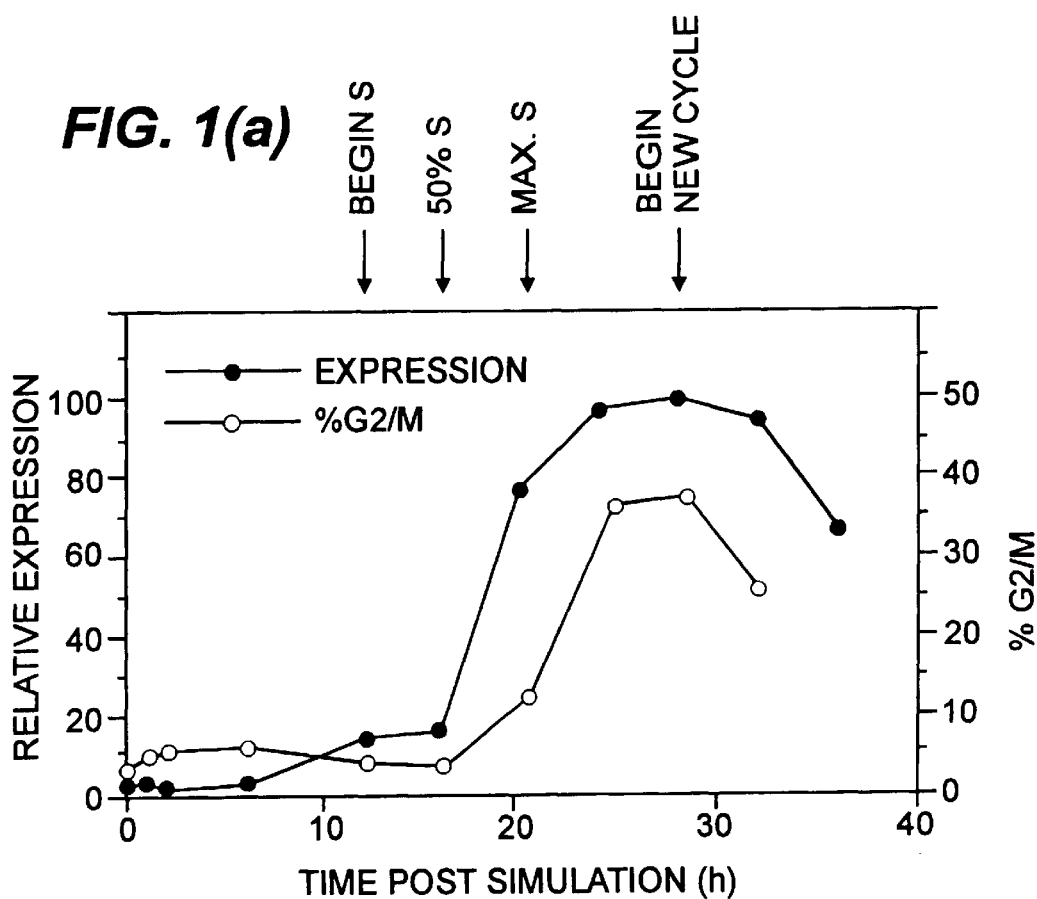

| EXP. | G0 (C74/C74R1) | | GROWING (C74/C74R1) | |
|---|---|---|---|---|
| A-I | 22/260 | → 11.8 | 202/459 | → 2.2 |
| A-II | 26/181 | → 7.0 | 897/688 | → 0.8 |
| A-III | 10/118 | → 11.8 | 268/546 | → 2.0 |
| A-IV | 8/122 | → 15.3 | 161/174 | → 1.1 |

| EXP. | G0 (C74/C74R1) | | G2 (C74/C74R1) | |
|---|---|---|---|---|
| B-I | 3/66 | → 21.7 | 65/171 | → 2.6 |
| B-II | 5/47 | → 9.4 | 104/78 | → 0.8 |

AVERAGE (±SD)    12.8±4.7                    1.6±0.7

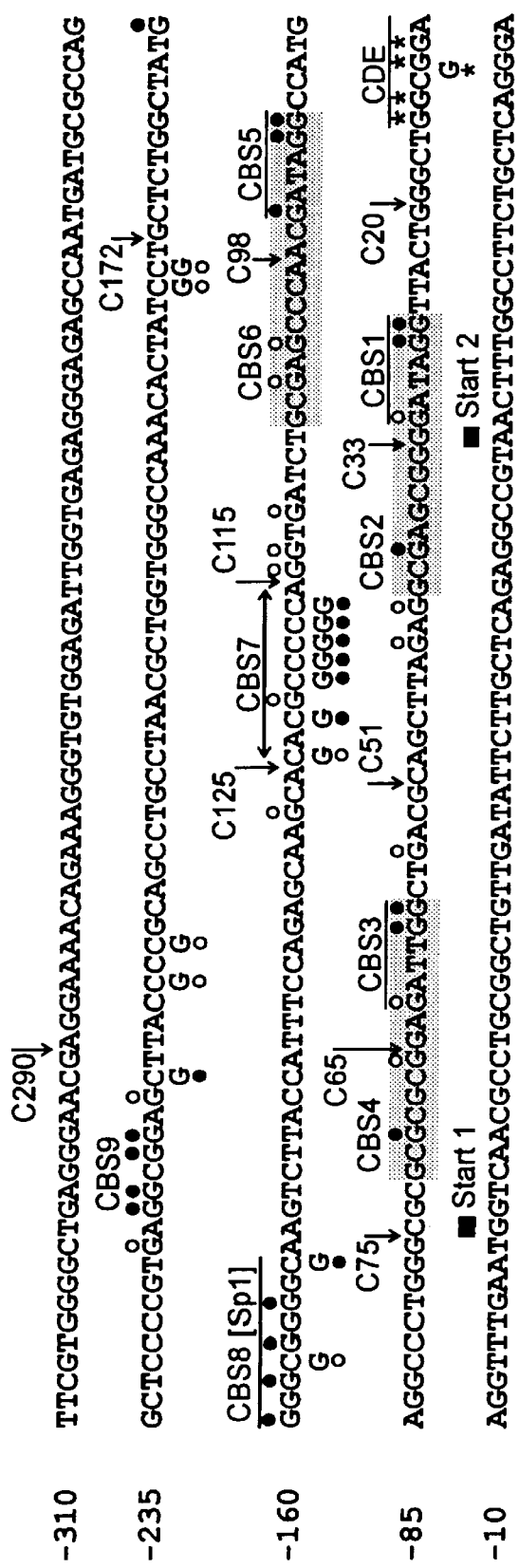

FIG. 15

|  |  | CDE | CHR |
|---|---|---|---|
|  |  | 1 2 3 4 5 6 7 8 9 10 |  |
| cdc25C | -20 | GGC TGGCGGAAG GTTTGAA |  |
| cdc2 | -26 | TTA GCGCGGTGA GTTTGAA |  |
| Cyclin A | -39 | TAG TCGCGGATA CTTGAA |  |
| Cyclin F | -89? | AGG GCCGGGTGC GTTTGAA |  |

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

GCTGGCGGAA GGTTTGAATG G                                    21

(2) INFORMATION FOR SEQ ID NO:2:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

CCCCTCGAGG TCAACTAGAT TGCAGC                               26

(2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

CGCCCCAACA CTTGCCACGC CGGCAGC                              27

(2) INFORMATION FOR SEQ ID NO:4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

CCCCTCGAGG TCAACTAGAT TGCAGC                               26

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

GGTTACTGGG CTGATCAAAG GTTTGAATGG                           30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

CCATTCAAAC CTTTGATCAG CCCAGTAACC                           30

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
AGGGAAAGGA GGTAGTT                                                17
```

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
TAGATTGCAG CTATGCCTTC CGAC                                        24
```

(2) INFORMATION FOR SEQ ID NO:9:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

```
CCTTCCGACT GGGTAGGCCA ACGTCG                                      26
```

(2) INFORMATION FOR SEQ ID NO:10:

(i) SEQUENCE CHARACTERISTICS:
        (A) LENGTH: 270 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
AGGCCTGGGC GCGCGCGGAG ATTGGCTGAC GCAGCTTAGA GGCGAGCGGG GATAGGTTAC    60
TGGGCTGGCG GAAGGTTTGA ATGGTCAACG CCTGCGGCTG TTGATATTCT TGCTCAGAGG   120
CCGTAACTTT GGCCTTCTGC TCAGGGAAGA CTCTGAGTCC GACGTTGGCC TACCCAGTCG   180
GAAGGCAGAG CTGCAATCTA GTTAACTACC TCCTTTCCCC TAGATTTCCT TTCATTCTGC   240
TCAAGTCTTC GCCTGTGTCC GATCCCTACT                                   270
```

(2) INFORMATION FOR SEQ ID NO:11:

(i) SEQUENCE CHARACTERISTICS:
        (A) LENGTH: 375 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

```
TTCGTGGGGC TGAGGGAACG AGGAAAACAG AAAGGGTGTG GAGATTGGTG AGAGGGAGAG      60
CCAATGATGC GCCAGGCTCC CCGTGAGGCG GAGSTTACSC SGCAGCCTGC CTAACGCTGG     120
TGGGCCAAAC ACTATSSTGC TCTGGCTATG GGGSGGGGSA AGTCTTACCA TTTCCAGAGC     180
AAGCASASGS SSSSAGGTGA TCTGCGAGCC CAACGATAGG CCATGAGGCC CTGGGCGCGC     240
GCGCGGAGAT TGGCTGACGC AGCTTAGAGG CGAGCGGGGA TAGGTTACTG GGCTGGSGGA     300
AGGTTTGAAT GGTCAACGCC TGCGGCTGTT GATATTCTTG CTCAGAGGCC GTAACTTTGG     360
CCTTCTGCTC AGGA                                                      375
```

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

```
GGCTGGCGGA AGGTTTGAA                                                  19
```

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
TTAGCGCGGT GAGTTTGAA                                                  19
```

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

```
TAGTCGCGGG ATACTTGAA                                                  19
```

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

```
AGGGCCGGGT GCGTTTGAA                                                  19
```

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

GCGCGCGGAG ATTGGCTGAC G                                              21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

CTGGGCTCTG ATTGGCTGCT T                                              21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

CTGTCGCCTT GAATGACGTC A                                              21

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

GGCGAGCGGG GATAGGT                                                   17

(2) INFORMATION FOR SEQ ID NO:20:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

CGGGCTACCC GATTGGT                                                   17

(2) INFORMATION FOR SEQ ID NO:21:

(i) SEQUENCE CHARACTERISTICS:
        (A) LENGTH: 17 base pairs
        (B) TYPE: nucleic acid
        (C) STRANDEDNESS: single -continued

```
            (D) TOPOLOGY: linear (ii) MOLECULE TYPE: DNA (xi) SEQUENCE DESCRIPTION: SEQ ID NO:21:

CGAGCGCTTT CATTGGT                                                     17

(2) INFORMATION FOR SEQ ID NO:22:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:22:

GGGCTGGCGG AAGG                                                        14

(2) INFORMATION FOR SEQ ID NO:23:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:23:

GCGCGCNNNG ATTGG                                                       15

(2) INFORMATION FOR SEQ ID NO:24:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:24:

GCGAGCNNNN NGATAGG                                                     17

(2) INFORMATION FOR SEQ ID NO:25:

(i) SEQUENCE CHARACTERISTICS:
            (A) LENGTH: 15 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:25:

GCGAGCNNNG ATAGG                                                       15
```

CELL CYCLE REGULATED REPRESSOR AND DNA ELEMENT

The present invention relates to a cell cycle regulated repressor protein which binds to a DNA element present in the control sequences of the human cdc25C gene and other cell cycle regulated genes, as well as the use thereof in cell cycle regulated expression systems.

Eukaryotic and prokaryotic cells replicate by a process of cell division in which the genome of the cell, be it a single molecule as in prokaryotes or a multiplicity of chromosomes as in eukaryotes, is precisely replicated before mitosis. Non-dividing, resting cells are in a phase known as G0. When undergoing division, the cell will move in to G1 phase, usually the longest phase, during which the DNA content is 2n (diploid). This is followed by S phase, in which DNA synthesis takes place and the genome is duplicated. A second G phase follows, G2, in which the cell is in a tetraploid (4n) state. Mitosis (M) then occurs, and the cell reverts to G0/G1. The G2→M transition, which involves cell and nuclear fission, is controlled by a mitosis promoting factor known as cdc2, and a cyclin (cyclin B). The human cdc25C gene encodes a protein phosphatase which activates the cdc2/cyclin B complex prior to the entry into mitosis.

cdc25C mRNA expression is largely restricted to the G2 phase and is developmentally controlled, but the mechanisms of its regulation have not been investigated prior to the present study. In fact, G2-specific transcription has previously not been analysed for any gene in mammalian cells. The molecular mechanisms underlying the periodic induction of genes in the G2 phase are therefore unknown.

cdc25 was originally discovered in *S. pombe* as a cell cycle gene with an essential function in G2→M progression (Russell and Nurse, 1986; for a review see Millar and Russell, 1992). Higher cells contain at least 3 genes with a high degree of similarity to cdc25, termed cdc25A, cdc25B and cdc25C, the latter being the closest kin of the *S. pombe* cdc25 (Millar et al., 1991; Nagata et al., 1991; Sadhu et al., 1990). It is now clear from a number of in vitro studies that the Drosophila, starfish and Xenopus cdc25C genes encode protein phosphatases which presumably directly activate the cdc2/cyclin B complex prior to entry into mitosis (Dunphy and Kumagai, 1991; Gautier et al., 1991; Millar et al., 1991; Sebastian et al., 1993; Strausfeld et al., 1991). In *S. pombe* cdc25 catalysis the dephosphorylation of Tyr-14 in cdc2, thereby reverting the inhibitory action of the wee-1 protein tyrosine kinase (Gould and Nurse, 1989). cdc2 in higher cells is phosphorylated on two residues upon formation of a complex with cyclin B, i.e., Tyr-14 and Thr-15 (reviewed in Millar and Russell, 1992). As in fission yeast, this inactivation of cdc2 is mediated by wee-1, which in mammalian cells has been reported to possess tyrosine and threonine kinase activity (Featherstone and Russell, 1991), and both Tyr-14 and Thr-15 are dephosphorylated by cdc25C (Gautier et al., 1991; Kumagai and Dunphy, 1991; Strausfeld et al., 1991). These observations demonstrate that cdc25 and cdc25C play crucial roles during cell cycle progression in many organisms by triggering the entry into mitosis.

In *S. pombe*, expression of the cdc25 gene is cell cycle-regulated and cdc25 mRNA and protein reach peak levels during G2 (Ducommun et al., 1990; Moreno et al., 1990). This regulation appears to be of particular relevance in view of the fact that the level of cdc25, unlike those of cdc2 or cyclin B, is rate-limiting with respect to entry into M-phase (Ducommun et al., 1990; Edgar and O'Farrell, 1989; Moreno et al., 1990; Russell and Nurse, 1986). In human cells, the level of cdc25C mRNA also increases dramatically in G2, but the abundance of cdc25 protein does not vary greatly during the cell cycle (Millar et al., 1991; Sadhu et al., 1990). The same applies to at least one of the cdc25 forms in *Xenopus oocytes* (Jessus and Beach, 1992).

Many diseases, for example cancer, are associated with aberrant cell proliferation.

Cancer is a disorder of the genetic make-up of somatic cells which results in a clone of cells with an abnormal pattern of growth control. This leads to unrestricted proliferation of the abnormal clone, which may present in the form of a tumour. Available therapy for cancer is based on the premise that cancer cells, being subject to unrestricted growth, undergo more frequent cell division than normal cells. Agents which target dividing cells are therefore seen as useful anti-cancer therapeutics. However, the effectiveness of such agents is limited, since their toxicity to normal cells precludes the administration of sufficiently effective doses. Moreover, within a tumour cell mass, a large proportion of the tissue is not rapidly dividing but is in a resting state. Therefore, even if all the dividing cells are eliminated, the tumour clone is not entirely ablated.

A refinement of such techniques which has been proposed is the use of antibodies or other cell-specific binding agents to target anti-cancer drugs specifically to tumour cells. For example, reference is made to the disclosures of EP 0 590 530 and EP 0 501 215 (Behringwerke AG) and references cited therein. A difficulty with the proposed techniques is that it has proven difficult to selectively target cancer cells over the background of normal tissue cells from which the cancer has developed, since tumour-specific antigens which are targeted by the antibodies or other binding agents are seldom truly tissue-specific.

Recently, gene therapy techniques have been proposed whereby expression systems encoding drugs or enzymes capable of activating prodrugs are targeted to cancer tissue, and preferably expressed selectively in transformed cells. This method allows the introduction of a further level of differentiation between tumour and normal tissues, by exploiting tumour-specific expression vectors as well as tumour-specific targeting systems.

As with antibody delivery systems, however, the drawback with selective expression systems is that background expression levels of the anti-cancer agent encoded by the expression system tend to be excessive, leading to destruction of non-transformed tissue. At the same time, it is difficult to achieve cancer-specific expression using currently available transcription regulation techniques, since qualitatively cancer cells seem to display very few useful differences from the normal tissue from which they derive.

It has now been found that the cdc25C gene and other cell cycle regulated genes, including cyclin A and cdc2 comprise a DNA element which binds a cell cycle specific repressor factor which, when bound, specifically represses transcription of the linked gene.

According to the first aspect of the invention, therefore, there is provided a vector for the expression of a desired gene product in a cell, comprising a structural gene encoding the desired gene product operably linked to a promoter under the control of a DNA repressor element which interacts with a cell cycle specific repressor in order to regulate gene expression in a cell cycle specific manner.

Preferably, the DNA repressor element is derived from a cell cycle regulated gene, such as the cdc25C gene and comprises at least part of the sequence 5'-GCTGGCGGAAGGTTTGAATGG-3' (SEQ ID NO: 1), or a functionally equivalent mutant or homologue thereof.

Alternatively, the DNA repressor element comprises the sequence 5'-GCTGGCGGAAGGTTTGAATGG-3' (SEQ ID NO: 1) and a sequence encompassing a transcription initiation site, or any functionally equivalent mutants or homologues thereof.

Preferably, the transcription initiation site is the sequence encompassing the first major transcription initiation site of the cdc25C gene.

The DNA repressor element is preferably derived from the cdc25C gene, the cdc2 gene or the cyclin A gene.

The vector of the invention is a nucleic acid vector which may comprise RNA or DNA. The vector may be of linear or circular configuration and adapted for episomal or integrated existence in the target cell. Vectors based on viruses, such as retroviral or adenoviral vectors, usually integrate in to the cell genome. Moreover, linear and circular DNA molecules are known to integrate into cell genomes, as set out in the extensive body of literature known to those skilled in the art which concerns transgenic animals.

Where long-term expression of the gene product is sought, integrating vectors are preferred. However, if only transient expression of the gene product is sufficient, non-integrating episomes may be used.

The vector of the invention allows the production of a desired gene product in a manner which is dependent on the cell cycle phase in which the target cell finds itself. For example, in the case of the cdc25C-derived DNA repressor element, the desired gene product will only be produced during S and G2 phase, as the target cell prepares for mitosis. If desired, therefore, the invention allows production of specific gene products in target cells only at specific stages of the cell cycle.

In a particularly preferred embodiment of the invention, the vector is used to encode a cytotoxic agent. Use of such an agent will lead to preferential ablation of cycling cells, which has applications in the therapy of cancer and other disorders involving aberrant cell proliferation.

The gene product encoded by the vector system may be, in its broadest sense, any polypeptide or ribonucleic acid. For example, the gene product may be a polypeptide of therapeutic utility, such as a cytokine or other protein capable of stimulating or modulating an immune response, or a cytotoxic or cytostatic polypeptide. In a preferred embodiment, the polypeptide may be a prodrug-activating enzyme (see Mullen, Pharmac., Ther. 63, 199, (1994)), such as HSV thymidine kinase (TK), capable of converting the non-toxic 6-methoxypurine arabinonucleosides to toxic phosphate derivatives, or cytosine deaminase, capable of converting 5-fluorocytosine to 5-fluorouracil (see Sikora, K., *Tibtech,* 11, 197–201, 1993). Other examples include β-lactamase, pyroglutamate aminopeptidase, galactosidase or D-aminopeptidase, for example as described in EP 0 382 411 or EP 0 392 745, an oxidase such as ethanol oxidase, galactose oxidase, D-amino acid oxidase or α-glyceryl-phosphate oxidase, for example as described in WO 91/00108, a peroxidase, for example as described in EP 0 361 908, a phosphatase, for example as described in EP 0 302 473, a carboxypeptidase, for example carboxypeptidase G2 as described in WO 88/07378, an amidase or a protease, or most preferably a glucoronidase, especially β-glucoronidase, for example as described in EP 0 590 530. Preferably, the gene encoding the desired gene product encodes a desired gene product, such as β-glucoronidase, fused to a signal sequence such as those found in immunoglobulins, to ensure its secretion or localisation to the cell surface.

Alternatively, the gene product may be a ribonucleic acid such as an antisense RNA or a therapeutic ribozyme capable of promoting the destruction of a particular RNA species in a cell. For example, antisense RNA and ribozymes may be targeted to the gene products of oncogenes. Alternatively, they may be used to ablate specific RNA species essential for the survival of the cell, thus acting as a cytotoxic or cytostatic agent. Moreover, ribonucleic acids may be used to target cellular DNA directly, preventing its expression in the cell.

A particularly preferred aspect of the invention is the construction of a chimaeric promoter that is active preferentially or specifically in the dividing cells of a specific lineage or tissue. This synthetic promoter comprises a tissue- or cell type-specific regulatory element in addition to the repressor element, and should also include the DNA sequence located immediately downstream of the repressor element which harbours the transcription initiation sites. Preferably, the tissue or cell type-specific regulatory element is positioned upstream of the repressor element. Alternatively, the repressor element may be inserted into the context of a complete transcription control unit of a tissue-specific gene. In order to achieve maximal repression in resting cells it may also be advantageous to insert into the chimaeric promoter multiple copies of the repressor element, preferably in a head-to-tail configuration. These strategies provide promoters with dual specificity, i.e. tissue- or cell type-specificity and the dependence on cell proliferation. Where the vector is useful in cancer therapy, the tissue-specific control elements are selected to be active in the tissue from which the tumour is derived and to retain their transcription activating function after malignant transformation. Ideally, tissue-specific regulatory elements should not be active in the proliferating, often undifferentiated cells of normal tissue. These criteria are fulfilled by, e.g., the tissue-specific regulatory elements in the sucrase isomaltase promoter. The combination of such a tissue-specific enhancer and a cell cycle-regulated repressor, such as that of the cdc25C promoter, allows the construction of a vector that drives transcription preferentially or specifically in tumour cells rather than in normal tissue.

The regulatory sequences referred to above include enhancers, which are preferably tissue specific and contribute to the restriction of the expression of the gene product to the target cell type. It is an advantage of the invention that enhancers may be used without compromising the cell cycle regulation of expression from the vector. If, unlike in the present invention, a cell cycle regulated activator were used, use of an enhancer would be precluded as this would raise the background level of transcription unacceptably. The use of a repressor, however, results in the negation of the effects of the enhancer when the vector is in the repressed state.

Moreover, the regulatory sequences contemplated for use with the invention include Locus Control Regions (LCRs) as described in EP 0 332 667. LCRs have the ability to promote integration-site independent expression of transgenes and are thus particularly useful where the vector of the invention is to be integrated in to the genome of the target cell, as they will ensure that the gene product will be expressed.

Examples of genes having regulatory sequences, including enhancers, useful for expressing anti-cancer gene products may be found in the relevant literature (e.g. see: Sikora et al., Ann. N.Y. Acad. of Sciences, 716, 115, (1994); Osaki et al., Cancer Res., 54, 5258, (1994); Dihaio et al., Surgery, 116, 205, (1994); and Harris et al., Gene Therapy, 1, 170, (1994). For example, in the case of colon adenocarcinoma, regulatory sequences derived from the carcinoembryonic antigen gene, the sucrase isomaltase gene, the glucagon gene, the villin gene or the aminopeptidase N gene may be used; for gastric and oesophageal adenocarcinoma, the sucrase isomaltase gene; for pancreatic carcinoma, the mucin-1 gene or the villin gene; for small cell lung carcinoma, the neuron-specific endolase gene or the DOPA decarboxylase gene; for lung adenocarcinoma, the surfactant protein A, B and C genes, the uteroglobulin/CC10 protein gene or the aminopeptidase N gene; for thyroid adenocarcinoma, the calcitonin gene or the thyroglobulin gene; for prostate carcinoma, the prostate-specific antigen gene; and for melanoma, the tyrosinase gene or the TRP-1 gene.

The promoter and control sequences, including the cell cycle regulated DNA suppressor element of the invention, may be combined with a coding sequence encoding the desired gene product and packaged in a delivery system for administration to the target cells. Examples of suitable delivery systems include viral delivery systems (see Sikora, K., Tibtech, 11, 197–201, 1993) which, broadly speaking, may be of retroviral, adenoviral, adeno-associated or any other suitable viral origin, and include virus-based systems such as virosomes. Moreover, non-viral delivery systems are suitable for use with the invention. Such delivery systems include non-targeted delivery systems such as liposomes. However, targeted delivery systems are preferred. Most preferred are receptor-ligand mediated uptake systems, particularly antibody targeted uptake systems. Suitable antibodies for use in such systems are particularly antibodies to tumour-associated antigens, such as antibodies to carcinoembryonic antigen, neural cell adhesion molecule, the EGF receptor, TAG72, gangliosides $GD_2$ and $GD_3$ and other antigens known in the art. The antibody may be a "natural" antibody such as IgG, or a synthetic antibody "fragment" such as Fab or Fv, or a single chain Fv (scFv), which is preferably a humanised antibody fragment comprising humanised constant regions combined with non-human CDRs, all of which fragments are described in the relevant literature.

Where the gene product encoded by the vector of the invention is a prodrug activating enzyme, the prodrug may be a cancer-specific prodrug. Alternatively, the prodrug may be an agent which, after activation, has a general cytotoxic or cytostatic activity. The latter embodiment is particularly useful in the treatment of tumours.

In a tumour, relatively few of the cells are dividing.

These cells will be ablated by the prodrug on activation. However, if the prodrug is capable of killing also a few cells surrounding the tumour cell, non-dividing tumour cells will also be hit, resulting in faster destruction of the tumour. Preferably, the prodrug, once activated, is relatively immobile or has a short half-life, such that it will not be transported in active form too far from the site of activation.

In a second aspect of the invention, there is provided a cell cycle regulated transcriptional repressor.

An example of such a repressor is a proteinaceous repressor which, in vivo, regulates the expression of a cdc25C gene, preferably of the human cdc25C gene as specifically exemplified herein a cdc2 gene or a cyclin A gene.

The repressor is preferably a protein or a complex of proteins. However, chemical analogues thereof, which are not necessarily proteinaceous but which have the same function, are envisaged.

The invention also comprises mutated or otherwise altered repressor-derived proteins or chemical analogues of the repressor which mimic or improve upon its activity. Where the repressor is one of a family of proteins, the differential activity thereof may be improved or altered.

The repressor of the invention functions in association with a DNA repressor element which binds specifically to the entity or entities comprising the repressor. In the case of the cdc25C repressor, this DNA repressor element is located upstream of, and overlaps, the cdc25C gene promoter and comprises at least part of the sequence 5'-GCTGGCGGAAGGTTTGAATGG-3' (SEQ ID NO: 1), or a functionally equivalent mutant or homologue thereof.

The invention further provides a nucleic acid sequence or sequences encoding the repressor, as well as an expression vector comprising such a nucleic acid sequence or sequences.

The nucleic acid sequence or sequences encoding the repressor may encode the entire repressor or at least one of the components of the repressor, or part of the repressor or part of at least one of the repressor components. Preferably the nucleic acid sequence or sequences are cDNA.

A complementary DNA (cDNA) encoding the repressor or components thereof can be isolated by screening a mammalian cDNA library constructed in a phage-based prokaryotic expression vector with a radioactively labelled oligonucleotide representing the repressor binding site according to established procedures known to those skilled in the art (Singh et al., 1988). The cDNA can be derived from any cell type or tissue where the repressor is expressed, such as human fibroblasts. Alternatively, a cDNA encoding the repressor or components thereof can be obtained by hybridising a mammalian cDNA library constructed in a phage-based vector to a radioactively labelled, synthetic oligonucleotide probe. This probe is deduced from the amino acid sequence of proteolytic fragments of the respective protein. Such fragments can be obtained by digesting the isolated protein with appropriate proteinases, such as trypsin, chymotrypsin or V8, and separation of the resulting fragments by high pressure liquid chromatography. These techniques as well as the micro-sequencing of polypeptides are described in a vast body of literature (e.g., Meyer et al., 1991) and known to those skilled in the art. Isolation of the repressor itself can be achieved by conventional biochemical purification procedures (ion exchange, hydrophobic and size exclusion chromatography) followed by affinity chromatography using an immobilised, multimeric repressor binding site according to published procedures (Briggs et al., 1986), known to those skilled in the art.

The invention further provides the use of the nucleic acid sequence or sequences, as well as an expression vector comprising such a nucleic acid sequence or sequences, in the production of the repressor protein, protein complex or parts thereof.

It is possible that the repressor will comprise a family of proteins, possibly tissue-specifically expressed, which have differing activities in different tissues. In such a situation, the invention comprises selecting the appropriate protein or proteins from the family in order to achieve the desired effect in the target tissue.

In a further aspect of the present invention the repressor protein, protein complex or parts thereof can be used in an assay for antagonists or agonists of the repressor function. Basically, by performing such an assay it is possible to identify substances that affect repressor action. Methods for identifying such antagonists or agonists are well known to those skilled in the art and are described in the body of literature known to those skilled in the art relating to such assays.

In a further aspect of the present invention the repressor protein, protein complex or parts thereof and enhancer binding proteins can be used in an assay for antagonists or agonists of the repressor function. Preferably, the enhancer binding proteins interact with the enhancer of the cdc25C gene and the equivalent regions of the cdc2 gene or the cyclin A gene. It is further preferred that the enhancer binding proteins are the glutamine-rich CCAAT-box binding proteins (such as NF-1/CTF) and Sp1 family members. Basically, by performing such assays it is possible to identify substances that affect repressor action by binding to either the repressor and/or the enhancer proteins. Methods for identifying such antagonists or agonists are well known to those skilled in the art and are described in the body of literature known to those skilled in the art relating to such assays.

The repressor of the invention can be exploited in a variety of ways, to influence expression of cell cycle regulated genes and therefore affect the cycling and growth of cells. This use is of relevance in the control of disorders and diseases which involve aberrant cell proliferation, as exemplified hereinafter. The repressor may be administered to target cells using an appropriate delivery system, such as a liposomal delivery system, in order to delay or prevent the onset of mitosis. Alternatively, nucleic acid encoding the repressor may be administered to the cells, again using a suitable delivery system, such as those known to persons skilled in the art and referred to hereinbefore, such that the repressor is produced in the target cells in situ.

In a further aspect, the invention provides a method for the treatment of a disease which is associated with aberrant cell proliferation comprising the administration to a target cell of a vector according to the second aspect of the invention, wherein the gene product is of therapeutic significance in the treatment of the disease.

Diseases amenable to treatment by the method of the invention include cancers of all types, but also other proliferation diseases. For example, the treatment of psoriasis is envisaged, as is the treatment of inflammatory disease, certain viral infections, especially virally-induced cancers and warts, where the virus is responsible for the deregulation of the cell cycle, fungal infections and proliferative heart disease.

The invention moreover provides a vector according to the second aspect of the invention for use in medicine.

Figure 1B:
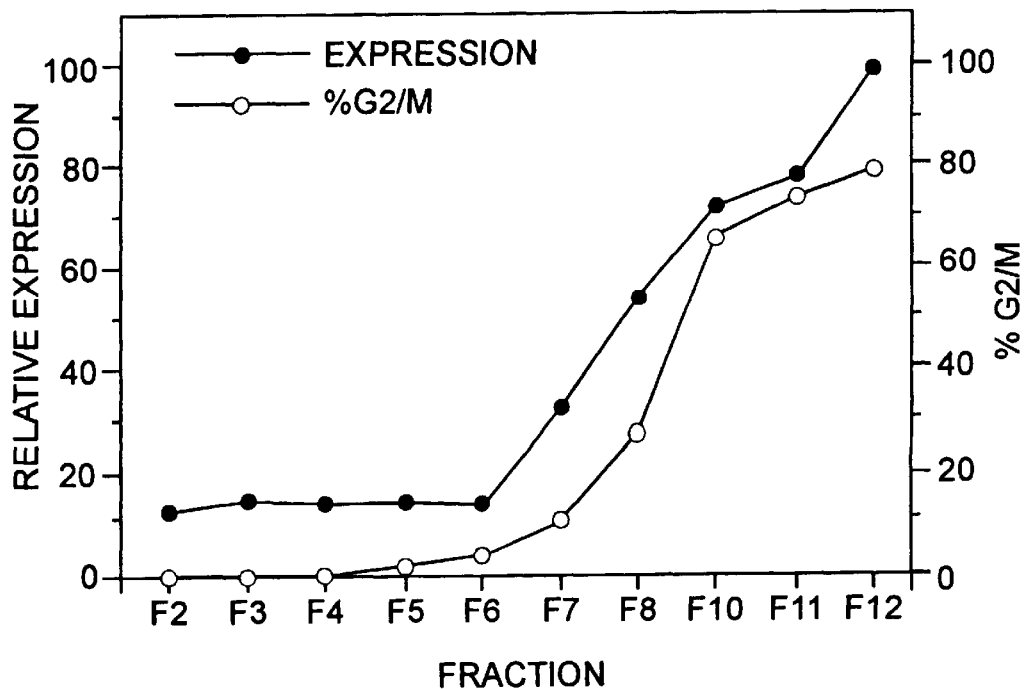

The invention is illustrated in the appended examples, with reference to the following figures:

FIGS. 1A and 1B

Cell cycle regulation of cdc25C in the human diploid fibroblast cell line WI-38 after serum stimulation of cells synchronised in G0 by serum deprivation (FIG. 1A), and in normally cycling HL-60 cells fractionated by counterflow elutriation (FIG. 1B).

FIG. 1a: Reverse PCR analysis of stimulated WI-38 cells. L7, whose expression is not cell cycle dependent, was used as an internal control. Times are intervals post-stimulation. Quantitation of the results was by β-radiation scanning (Molecular Dynamics PhosphorImager). Relative mRNA cdc25C expression and the fraction of G2 cells as determined by FACS analysis are plotted against the time post-stimulation.

FIG. 1b: Expression of cdc25C mRNA in elutriated HL-60 cells determined as in panel a. G: non-fractionated cells; F2 . . . F12: fractions collected by counterflow elutriation. Quantitation of the results was by β-radiation scanning and cell cycle analysis as in panel a.

FIG. 2

Nucleotide sequence (SEQ ID NO: 10) of the human cdc25C gene around the transcription start sites. The two major sites of transcription initiation are marked by a solid square (see also FIG. 3). Protected G residues detected by in vivo footprinting (see FIG. 5) are marked by filled circles ( constitutive binding sites 1, 2 and 3: CBS 1, 2 and 3) or triangles (cell cycle dependent element: CDE). The 5' ends of the C74 promoter construct used in FIGS. 4B, 5 and 7 are shown by arrows pointing to the right; the common 3' end of all deletion constructs is indicated by an arrow pointing to the left.

FIG. 3

Mapping of the 5' end of cdc25C mRNA by primer extension in normally cycling WI-38 cells (leftmost lane). Control: E. coli tRNA (negative control) A sequencing reaction was run alongside to be able to accurately determine the 5' ends of cdc25C MRNA. The two major sites of transcription initiation are indicated by arrows.

Figure 4A:
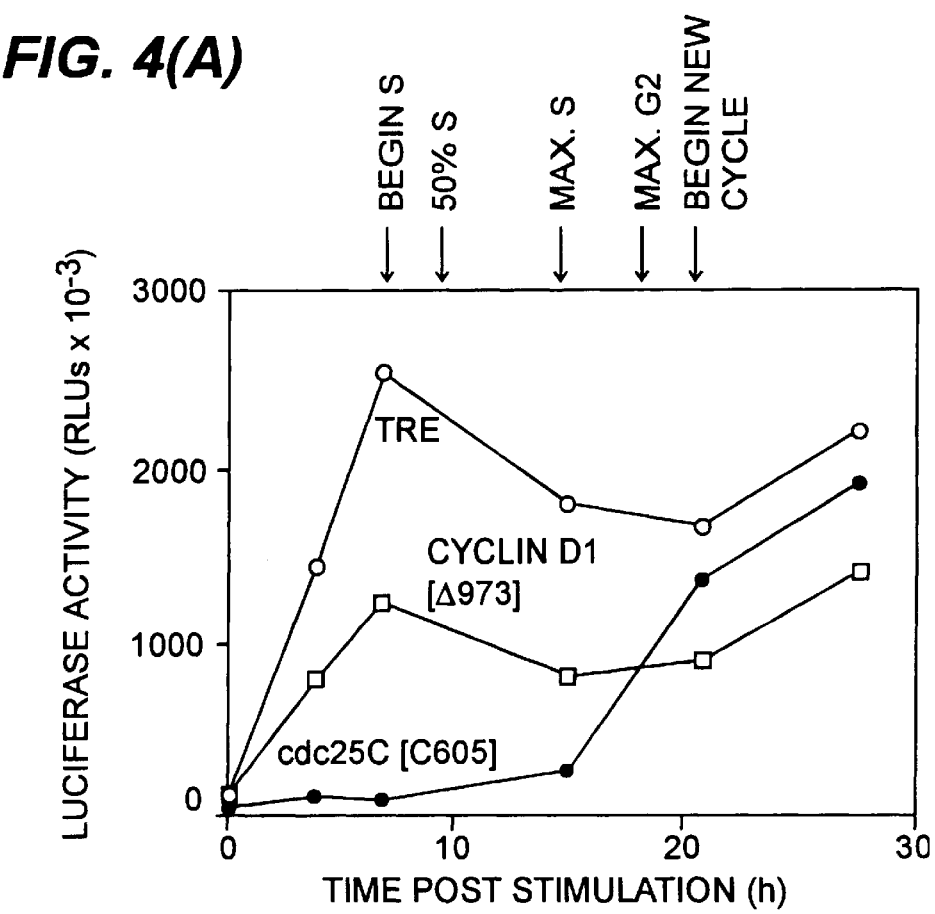
Figure 4B:
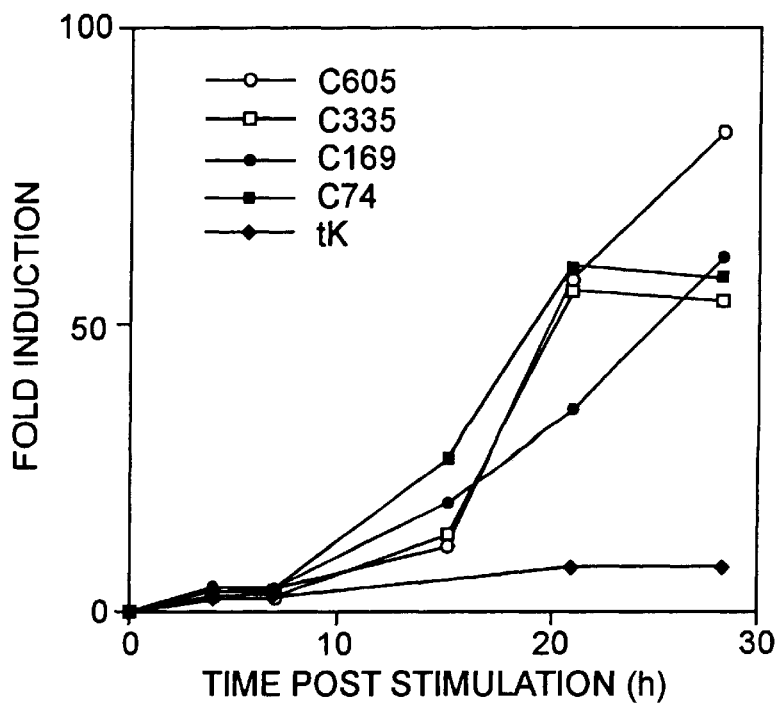

FIGS. 4A and 4B

Kinetics of induction after serum stimulation of quiescent NIH3T3 cells of different promoter-luciferase constructs: 5×TRE-tk ("TRE"), 973 bp of the human cyclin D1 promoter ("Δ973": Herber et al., 1994) and a 605 bp human cdc25C upstream fragment in FIG. 4A, and of different truncated cdc25C promoter constructs in FIG. 4B, which also shows the results obtained with the HSV tk-promoter for comparison. Panel A gives the measured activities (RLUs), panel B shows the level of induction for each construct tested (i.e., values relative to activity in $G_0$ cells).

Figure 5A:
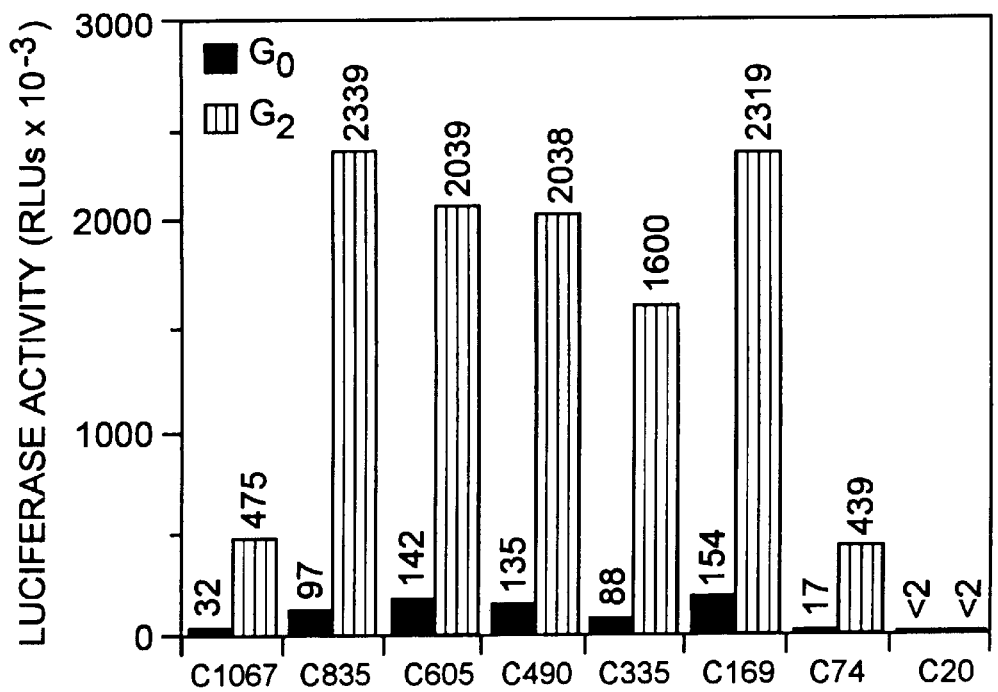
Figure 5B:
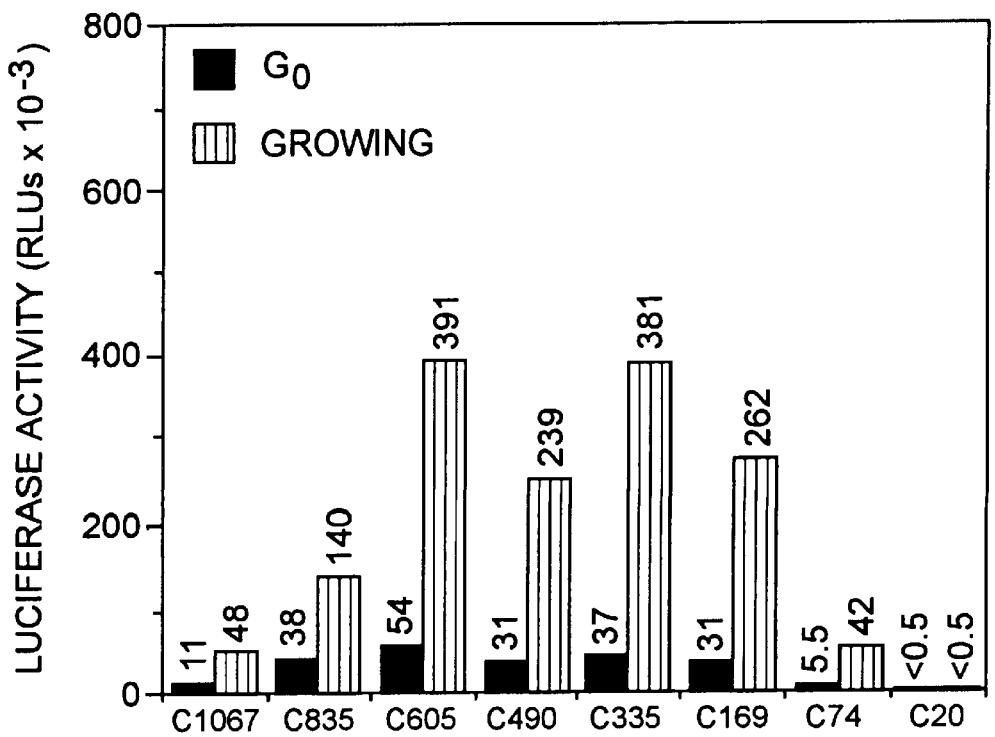

FIGS. 5A and 5B

Transient expression analysis of terminally truncated cdc25C promoter-luciferase constructs in quiescent ($G_0$) versus stimulated ($G_2$) NIH3T3 cells (FIG. 5A), and in quiescent ($G_0$) versus normally cycling (growing) cells (FIG. 5B). The stimulated cells were analysed 26 h post-stimulation, i.e. the majority of these cells were in $G_2$.

Experiments were performed 4-times with 2 independently prepared sets of plasmids. Relative activities of the different deletion constructs showed standard deviations in the range of 5–30%. Mean values and standard deviations are not indicated in this Figure. to be able to show the actual luciferase activities rather than normalised values.

FIG. 6A and 6B

Figure 6A:
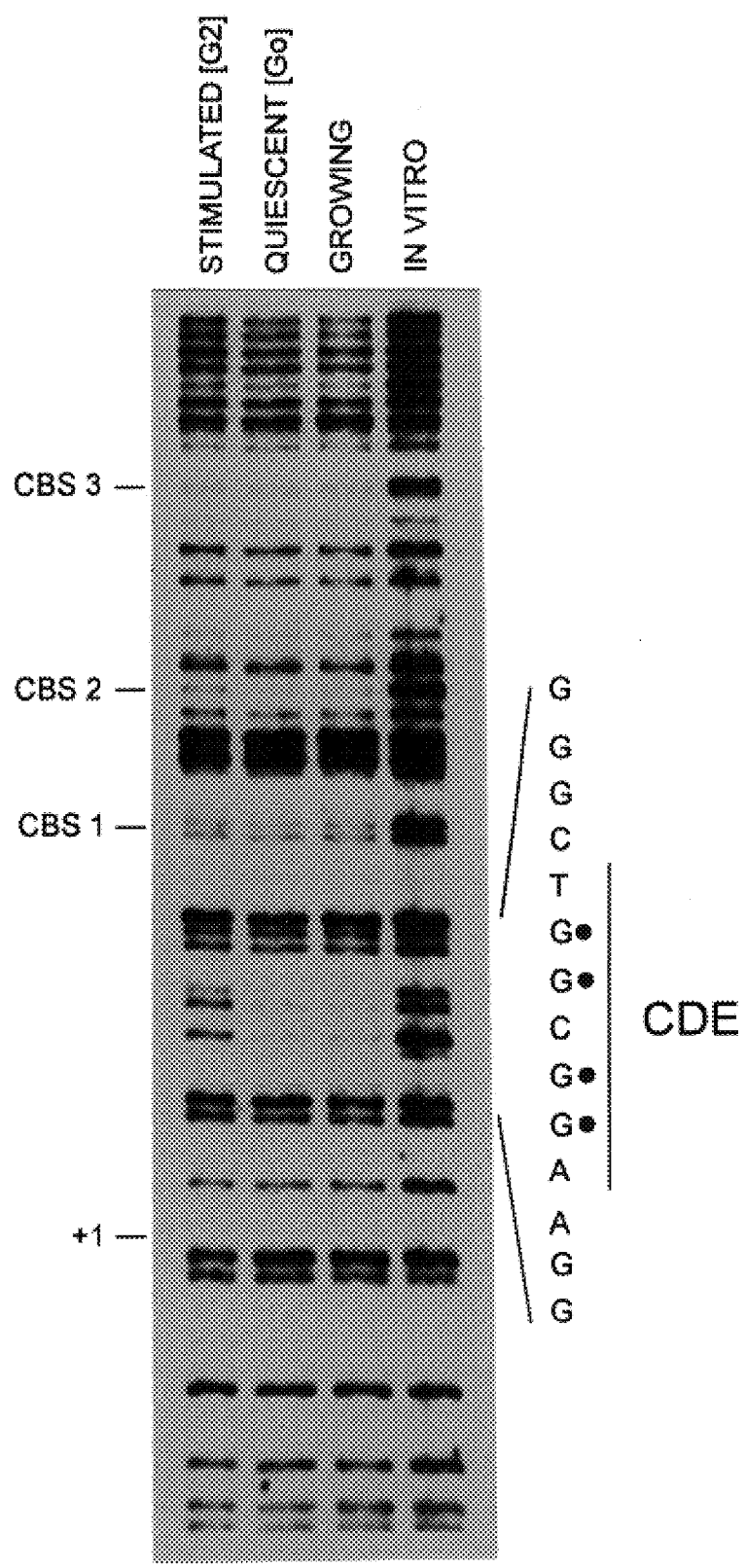

Identification of protein binding sites in WI-38 cells by in vivo DMS footprinting of a region spanning nucleotides −90 and +20 in FIG. 6A and nucleotides −21 and +8 in FIG. 6 B. One $G_2$-specific binding site (CDE) (located within SEQ ID NO: 22) and 3 constitutive binding sites (CBS 1, 2 and 3), which are protected under all growth conditions, can be identified. All protected G residues are marked in the sequence shown in FIG. 2. Control: naked DNA methylated in vitro. A: Quiescent, stimulated and growing WI-38 cells. The stimulated cells were 24 h post-stimulation, i.e. the majority of these cells were in $G_2$. B: Independent repetition of the experiment in panel A plus $G_1$ and $G_2$ cells isolated by FACS from populations of normally cycling WI-38 cells.

Figures 7A, 7B:
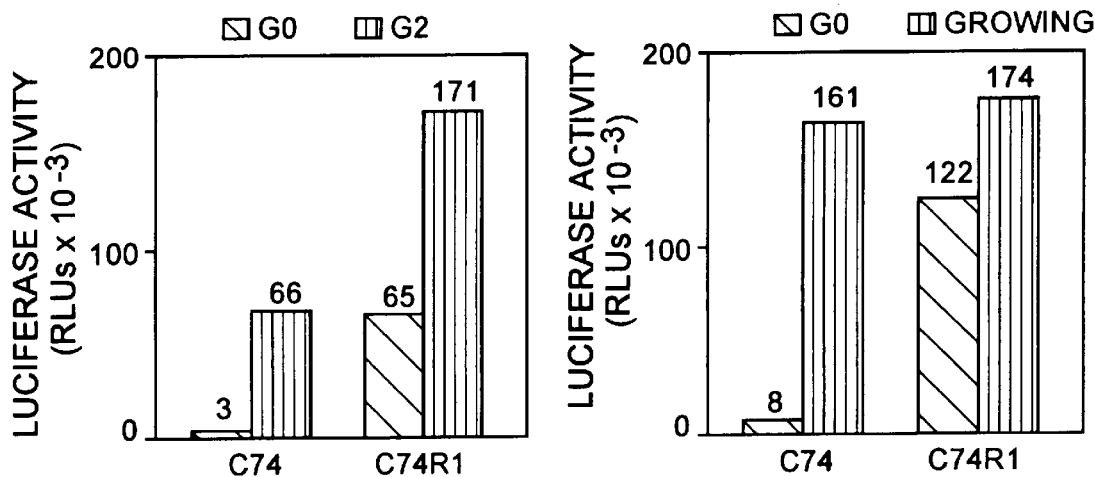

FIGS. 7A and 7B

Transient expression analysis of a cdc25C promoter-luciferase construct containing a mutated CDE (construct C74R1) in quiescent ($G_0$) versus stimulated ($G_2$) NIH3T3 cells (FIG. 7A, left graph) and in quiescent ($G_0$) versus growing cells (panel A, right graph). The CDE sequence was mutated as follows: . . . CT<u>GGCGG</u>AA . . . → . . . CTG AT<u>CAAA</u> . . . (protected G residues underlined; mutated bases double-underlined). FIG. 7B shows the results obtained in 6 independent experiments. Values separated by slashes indicate luciferase activities obtained with C74 (left value) and V74R1 (right value), respectively, under different growth conditions (top panel: $G_0$ and growing; bottom panel: $G_0$ and $G_2$). The increase in promoter activity caused by the CDE mutation is also indicated for each pair of values (fold increase). Averages and standard deviations for $G_0$ and

9

$G_2$/growing cells are shown at the bottom, indicating that mutation of the CDE in C74R1 led to an average 12.8-fold increase in $G_0$ cells, but only to 1.6-fold increase in $G_2$/growing cells.

FIGS. 8A and 8B

FIG. 8A) Nucleotide sequence (SEQ ID NO: 11) of the cdc25C upstream region. The two major sites of transcription initiation are marked by a solid square. Protected G residues detected by in vivo footprinting are marked by filled (•) and open (○) circles to denote strong and partial constitutive protection, respectively. Cell cycle-regulated protein binding to the CDE is indicated by asterisks. $Y_c$-boxes 1, 2 and 3 are shaded, $Y_c$-box 1 being the most downstream one. Arrows show the 5' end points of the deletion constructs used in subsequent Figures. FIG. 8B) Alignment of $Y_c$-boxes 1 (SEQ ID NO: 25), 2 (SEQ ID NO: 24) and 3 (SEQ ID NO: 23). Filled and open circles indicate G residues that show strong (•) or partial (○) protection in all three sequences.

FIG. 9

Transient expression analysis of terminally truncated cdc25C promoter-luciferase constructs in quiescent ($G_0$) versus growing NIH3T3 cells. Plasmids were named to indicate the 5'-truncation (see also FIG. 8). All plasmids harbour a 121 bp region downstream of the first initiation site. Mean normalised values (C290 in growing cells=100%) of 3 independent experiments and standard deviations are given. Factor is the ratio of the values in growing and $G_0$ cells. Δ Site indicates which site was deleted from a given construct with respect to the preceding one (one line above). Arrow heads point to those sites whose deletion led to a significant drop in activity (≥30%).

FIGS. 10A and 10B

Transient expression analysis in quiescent ($G_0$) and growing NIH3T3 cells of cdc25C promoter-luciferase constructs harbouring specific mutations in CBS elements. Black boxes: CBS elements in $Y_c$-boxes; grey boxes: other non-mutated elements; open boxes: mutated CBS elements. The analysis and evaluation was performed as in FIG. 9.

FIG. 11

Transient expression analysis in quiescent ($G_0$) and growing NIH3T3 cells of various cdc25C enhancer fragments linked to the C20 basal promoter construct with either a wild-type or a point-mutated (RT7 constructs) CDE. Black boxes: CBS elements in $Y_c$-boxes; grey boxes: other non-mutated elements; open boxes: mutated CDE (RT7 mutants). The analysis and evaluation was performed as in FIG. 10.

FIG. 12

Mutagenesis of the CDE. Constructs were tested in both quiescent and growing NIH3T3 cells.

FIG. 13

Mutagenesis of the region between the CDE and position +30. Constructs were tested in both quiescent and growing NIH3T3 cells. φ: no significant difference in activity of wt and mutant form in quiescent cells; +++: 3- to 10-fold deregulation; arrow: −2-fold decreased activity. No major differences were seen in growing cells.

FIG. 14

Repression of the SV40 early promoter/enhancer region by the CDE in transient luciferase assays. SV-TATA: A natural SV40 construct containing the SV40 early promoter/enhancer region, TATA-box and transcription start site. SV-C20: fusion construct consisting of the SV40 early promoter/enhancer region linked to a minimal cdc25C promoter fragment (−20 to +121) harbouring a wild-type CDE. SV-C20R1: same as SV-C20, but with a mutated CDE. All constructs were tested in quiescent ($G_0$) and growing cells. Data were normalised to 100 for SV-TATA in $G_0$ cells.

FIG. 15

Similarities of cell cycle-regulated promoters in the region of the CDE and CHR. cdc25C (SEQ ID NO: 12), cdc2 (SEQ ID NO13), Cyclin A (SEQ NO: 14), Cyclin F (SEQ ID NO: 15).

FIG. 16

Similarities of the cdc25C (SEQ ID NOS: 16 and 19), cdc2 (SEQ ID NOS: 17 and 20) and cyclin A (SEQ ID NOS: 18 and 20) promoters in the region of the CDE-CHR elements and upstream sequences resembling reverse CCAAT boxes (Y-boxes 1 and 2 in the cdc25C gene).

Materials and Methods

Library Screening

A genomic library of the human lung fibroblast cell line WI-38 constructed in 1-Fix (Stratagene) was screened with a $^{32}$P-labelled cdc25 CDNA probe (Sadhu et al., 1990) cloned by reverse PCR. Hybridisation was carried out for 24 h at 60° C. in 5×SSC, 0.1% SDS, 5×Denhardts solution, 50 mM sodium phosphate buffer pH 6.8, 1mM sodium phosphate and 200 μg salmon sperm DNA per ml. Filters (Pall Biodyne A) were washed at the same temperature in 0.1% SDS and 0.1% SSC.

Primer Extension Analysis 32P-labelled primer (10 pmol) and total RNA from HeLa cells were denatured for 10 min at 65 ° C. and then incubated at 370° C. for 30 min. Primer extension was carried out in a total volume of 50 μl containing 50 mM Tris pH 8.3, 75 mM KCl, 10 mM dithiothreitol, 3 mM MgCl$_2$, 400 μM dNTPs, 2 U RNasin and 400 U M-MuLV reverse transcriptase (Gibco-BRL). After incubation for 1 hr at 37° C., the reaction was stopped with EDTA followed by an RNase treatment. The precipitated DNA was subsequently electrophoresed on a 6% acrylamide/7M urea gel. The following 5' primer was used:

5'-CCCCTCGAGGTCAACTAGATTGCAGC-3' (SEQ ID NO: 2).

Exonuclease III Treatment

For sequence analysis, 5' deletions of a genomic AccI/EcoR1 fragment were performed by exonuclease III digestion using a nested deletion kit (Pharmacia-LKB).

PCR Mutagenesis

Site directed mutagenesis was performed as described (Good and Nazar, 1992) with slight modifications. Two complementary primers carrying the mutation and an additional restriction site plus a second set of primers for subcloning were designed. The first PCR reaction (Saiki et al., 1988) was performed with (i) 5'cdc25 and 3'mCDE and (ii) 3'cdc25 and 5'mCDE as the primers. The resulting products were purified (QIAquick spin PCR purification; Diagen), digested with the enzyme for the newly created restriction site, ligated and amplified in a second PCR reaction using 5'cdc25 and 3'cdc25 as primers. The resulting fragments carrying the mutation were cloned into the corresponding restriction sites of the cdc25 promoter-luciferase construct. The mutant was verified by sequencing. The primers had the following sequences:

5'cdc25, 5'-CGCCCCAACACTTGCCACGCCGGCAGC-3' (SEQ ID NO: 3); 3'cdc25', 5'-CCCCTCGAGGTCAACTAGATTGCAGC-3' (SEQ ID NO: 4); 5'MCDE, 5'-GGTTACTGGGCTGATCAAAGGTTTGAATGG-3' (SEQ ID NO: 5);
3'mCDE,
5'-CCATTCAAACCTTTGATCAGCCCAGTAACC-3' (SEQ ID NO: 6).

Reverse Transcriptase PCR

For cDNA synthesis, 4 μg of total RNA (Belyavsky et al., 1989) were annealed to 1 μg of oligo(dT) and incubated with 200 U of M-MuLV reverse transcriptase for 1 h at 37° C. in a final volume of 20 μl. One tenth of the reaction mixture was amplified by 17–25 cycles of PCR (Saiki et al., 1988) in the presence of 0.5 μCi α-$^{32}$P-dCTP. The PCR products were quantitated by β-radiation scanning using a PhosphorImager (Molecular Dynamics).

Cell Culture and DNA Transfection

WI-38 cells were obtained from the ATCC. All cells were cultured in Dulbecco-Vogt modified Eagle medium supplemented with 10% fetal calf serum (FCS), penicillin (100 Uml$^{-1}$) and streptomycin (100 Uml$^{-1}$). NIH3T3 cells were transfected using the calcium phosphate technique. 1×10$^5$ cells/dish (3 cm diameter) were plated 24 hrs prior to the transfection of 5 μg of DNA. Cells were harvested by scraping and lysed by three freeze-thaw cycles. For serum stimulation, cells were maintained in serum free medium for 3 days. Stimulation was carried out for the indicated times with 10% FCS. Luciferase activity was determined as described (Heiber et al., 1992). Results were corrected for transfection efficiency as described (Abken, 1992).

Genomic Footprinting

For genomic footprinting (Pfeifer et al., 1989), WI-38 cells were grown to 70% confluency. The cells were treated with 0.2% dimethyl sulfate (DMS) for 2 min. After DMS treatment, cells were washed three times with cold PBS, and the DNA was isolated. As a reference, WI-38 genomic DNA was methylated in vitro with 0.2% DMS for 10–30 seconds. Piperidine cleavage was performed as described. For FACS analysis and sorting, the cells were trypsinised after DMS treatment, resuspended in PBS and fixed in 70% ethanol overnight at 4° C. The fixed cells were washed twice with cold PBS and resuspended in 5 ml DNA staining buffer (100 mM Tris pH 7.4, 154 mM NaCl, 1 mM CaCl$_2$, 0.5 mM MgCl$_2$, 0.1% NP40, 0.2% BSA, 2 μg/ml Hoechst 33258). Cell sorting was performed with a Becton-Dickinson FACStar Plus at a rate of 500–1000 cell/sec. The sorted G1 and G2 cell populations were ~90% and ~80% pure, respectively. The genomic DNA from sorted cells was purified on anion exchange columns (QIAamp, Qiagen). 3 μg genomic DNA were used for ligation mediated PCR (LMPCR) as described. The Stoffel fragment of Taq polymerase (Perkin Elmer) was used instead of the native enzyme.

Samples were phenol extracted and ethanol-precipitated before primer extension with $^{32}$P-labelled primers. The following oligonucleotides were used as primers: LMPCR 1 (this Figure): 1st primer, Tm=56.0° C., 5'-d(AGGGAAAGGAGGTAGTT)-3' (SEQ ID NO: 7); 2nd primer, Tm=74.0° C., 5'-d(TAGATTGCAGCTATGCCTTCCGAC)-3' (SEQ ID NO: 8); 3rd primer, Tm=83.0° C., 5'-d(CCTTCCGACTGGGTAGGCCAACGTCG)-3' (SEQ ID NO: 9).

Results

Induction of cdc25C mRNA Expression in G2 in Both Stimulated and Normally Cycling Cells The cdc25 gene has previously been shown to be expressed specifically in the G2 phase in HeLa cells. In order to investigate whether the G2 specific expression of cdc25 mRNA is a general phenomenon in human cells we analysed both WI-38 cells synchronised by serum deprivation and stimulation, and normally cycling HL-60 cells fractionated by counter-flow elutriation. cdc25C RNA levels were quantitated by reverse PCR and cell cycle progression was determined by FACS analysis. The results of this study (FIG. 1) show that in both cell types and under both experimental conditions expression of cdc25c RNA was clearly G2 specific. Thus WI-38 cells began to enter G2 approximately 20 hrs post-stimulation which coincides with the time when the level cdc25C PNA increased. Similarly, the fraction of G$_2$/M cells in different samples of HL-60 cells obtained by counter flow elutriation closely correlated with the expression of cdc25C RNA. The induction cdc25C was approximately 50-fold in stimulated WI-38 cells and about 10-fold in elutriated HL-60 cells. The higher induction in the stimulated WI-38 cells is presumably due to a lower basal level in quiescent versus G1 cells.

Structure and Function of the Human cdc25C Gene 5' Flanking Sequence

Figure 2:
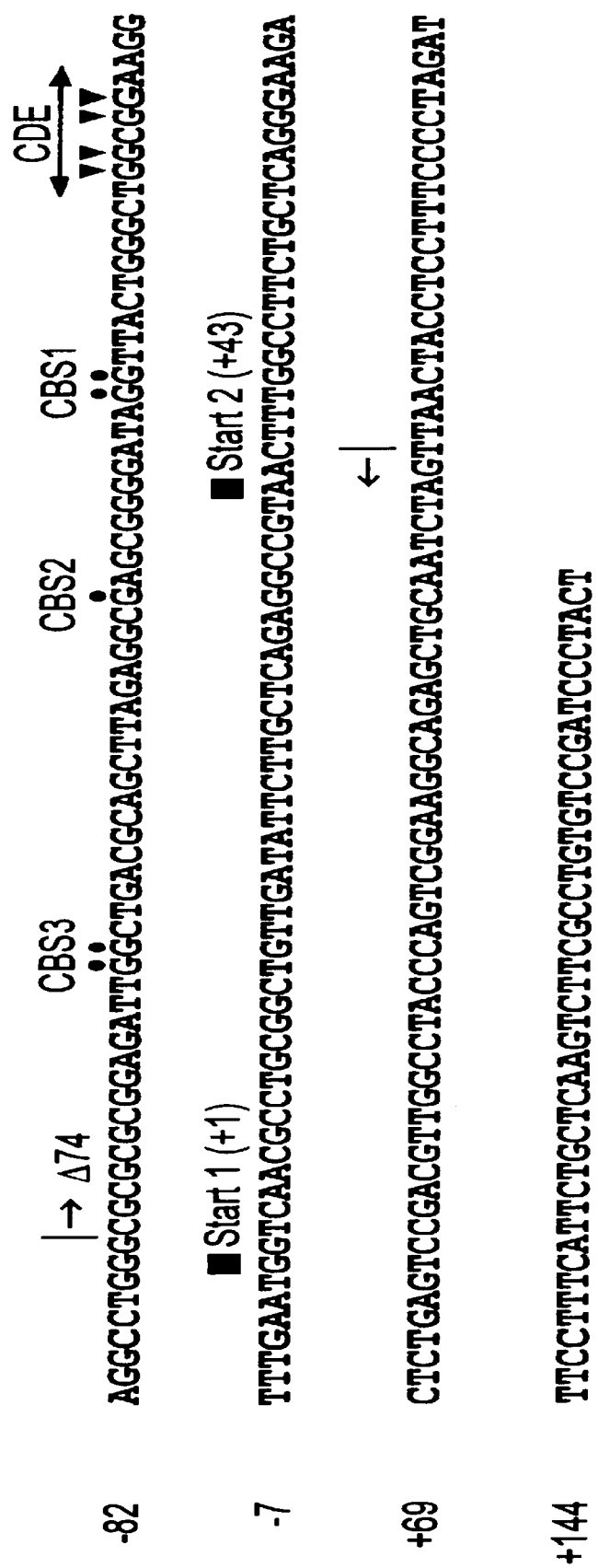
Figure 3:
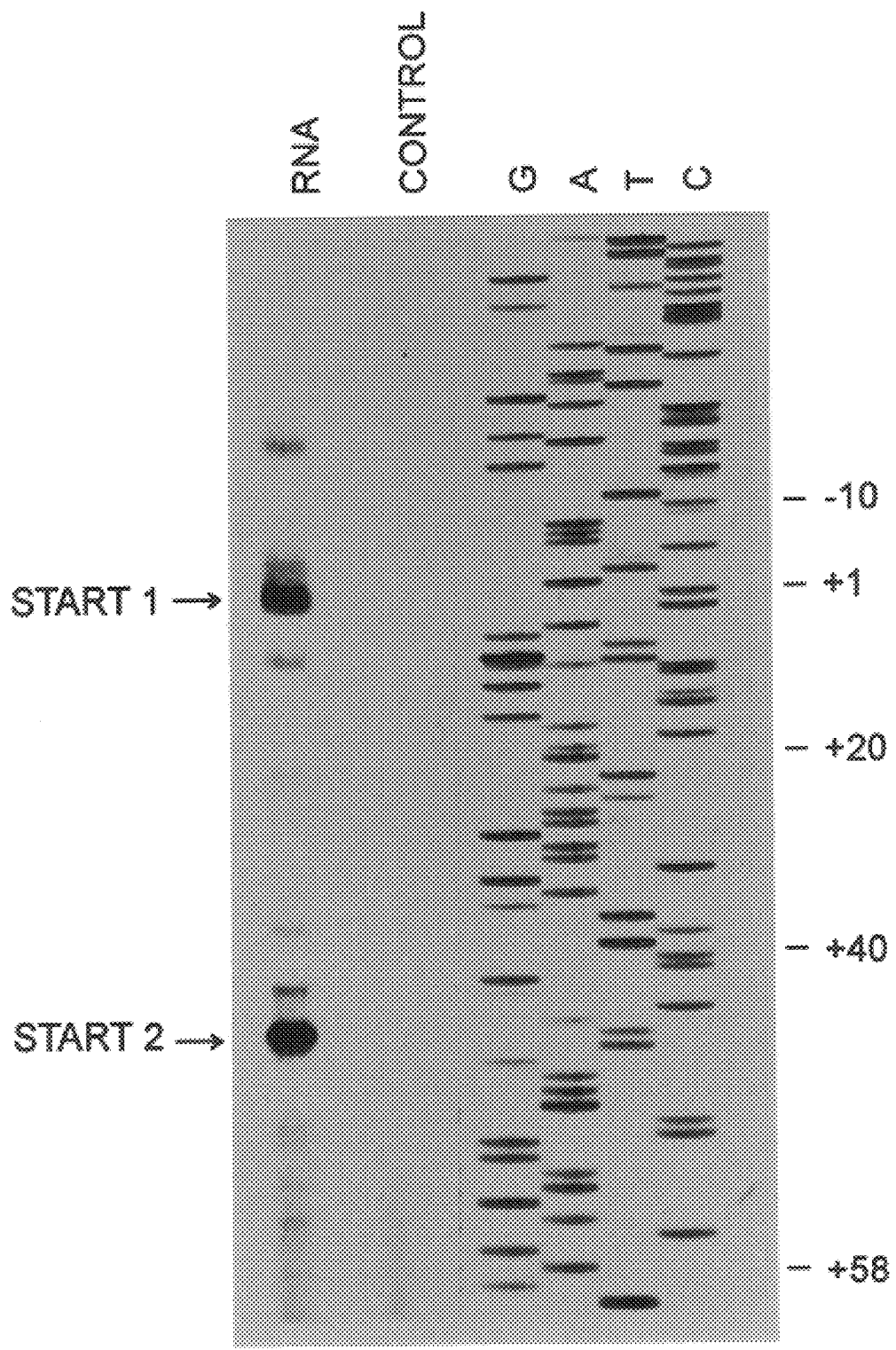

A genomic library of WI-38 cells was screened with a cDNA clone representing the human cdc25C coding region. A recombinant phage containing a 15 kb insert was identified and used for further analysis. The nucleotide sequence of approximately 1800 bp of the 5' flanking region was determined for both strands. The most relevant part of the sequence, as determined below, is shown in FIG. 2. To identify the point(s) of transcription initiation the 5' ends of cdc25C mRNA were determined by primer extension analysis (FIG. 3). This experiment led to the identification of two major start points located 227 and 269 bp 5' to the ATG start codon. Since the cdc25C gene is expressed in G$_0$/G$_1$ at extremely low levels (see FIG. 1), it was not feasible to analyse a potential cell cycle dependent usage of the two start sites. Inspection of the nucleotide sequence 5' to the start sites showed no canonical TATA box or TATA-like sequence, indicating that cdc25C is a TATA-less gene.

A cdc25C gene fragment spanning nucleotides −605 to +121 was linked to the bacterial luciferase gene (construct C605) and transfected into NIH3T3 cells to test whether the isolated promoter fragment was functional in a transient expression assay. Transfections were performed with relatively dense cultures which proved to be advantageous for two reasons: (i) The cells became quiescent more rapidly and efficiently compared with sparser cultures, and (ii) the protein content in quiescent, cycling and stimulated cells varied by a factor of ≦1.5 (data not shown), so that it was possible to correlate the measured luciferase activity directly to the number of transfected cells (the results were expressed as RLUs/2×10$^5$ recipient cells). Transfection efficiencies were monitored by determining the number of plasmids taken up by the cells (Abken 1992), but in general fluctuations were <1.5-fold (not shown). We prefer this experimental design over the cotransfection of a second reporter plasmid as an internal standard, because using the former approach we avoid complications with respect to serum stimulation of the reporter construct used for standardisation (which is seen to some extent even with promoters like RSV-LTR or SV40).

As shown in FIG. 4A, construct C605 was cell cycle regulated in serum stimulated cells that had been synchronised in G$_0$. Thus, hardly any luciferase activity was detectable in G$_0$ cells and during the first 15 hours post-stimulation, i.e. during G1 and early/mid-S, but there was a strong induction at 20 and 28 hrs. after serum stimulation, when most cells had entered, or passed through, $G_2$. In the same experiment we included two other reporter constructs containing either 5 copies of the human collagenase TRE linked to the HSV-tk promoter (Angel et al., 1987) or a 973 bp fragment of the human cyclin D1 promoter (Herber et al., 1994). Both the activation of AP-1 and the induction of cyclin D1 transcription are early events following serum stimulation, occurring prior to S-phase entry (e.g. Kovary and Bravo 1992; Sewing et al., 1993). This feature of the endogenous genes is reflected by the transient assay in FIG. 4A. Both the TRE and cyclin D1 promoter constructs gave rise to peak luciferase activities at approximately 7 hrs., i.e. prior to S-phase entry of the majority of the cell population. These data demonstrate that the transient expression assay closely mirrors the physiological regulation of the cdc25C gene and is sufficient to confer on a luciferase reporter gene a pattern of cell cycle regulation that is similar to that of the endogenous gene.

The level of C605 induction was ~50-fold in the experiment shown in FIG. 4A, but showed some variation in different experiments in the range of ~10- to 50-fold. Likewise, the level of luciferase activity in quiescent cells varied among different experiments (see FIGS. 5A and B). These variations, which are presumably due to unknown factors affecting the condition of the recipient cells at the time of transfection, have however no bearing on the interpretation of the results obtained in the present study, since relative activities comparing different constructs (e.g., terminal cdc25C promoter deletions, see below) within a given experiment were always very similar with variations <30%.

Identification of a 74 bp Promoter Fragment Conferring Cell Cycle Regulation

In order to identify functionally relevant regions in the cdc25C promoter we generated a series of terminal truncations and analysed these for expression in cells synchronised in $G_0$ versus stimulated cells in $G_2$ (FIG. 5A), and in $G_0$ versus normally cycling cells (FIG. 5B). In addition, two longer promoter fragments than the one analysed in FIG. 4A were analysed. The data in FIG. 5 shows that all constructs apart from C20, which contains just 20 nucleotides of upstream sequence, were clearly cell cycle-regulated, in both stimulated and normally cycling cells. This suggests that the sequence upstream of nucleotide −74 only plays a minor role, if any, in cell cycle regulation. This conclusion is strongly supported by the data in FIG. 4B which show that the induction kinetics of the four constructs tested, including C74, are very similar. The fact that even C74 showed the expected cell cycle-dependent expression pattern indicates that the region from −74 to +121 is sufficient for late S/G2-specific transcription.

Figure 9:
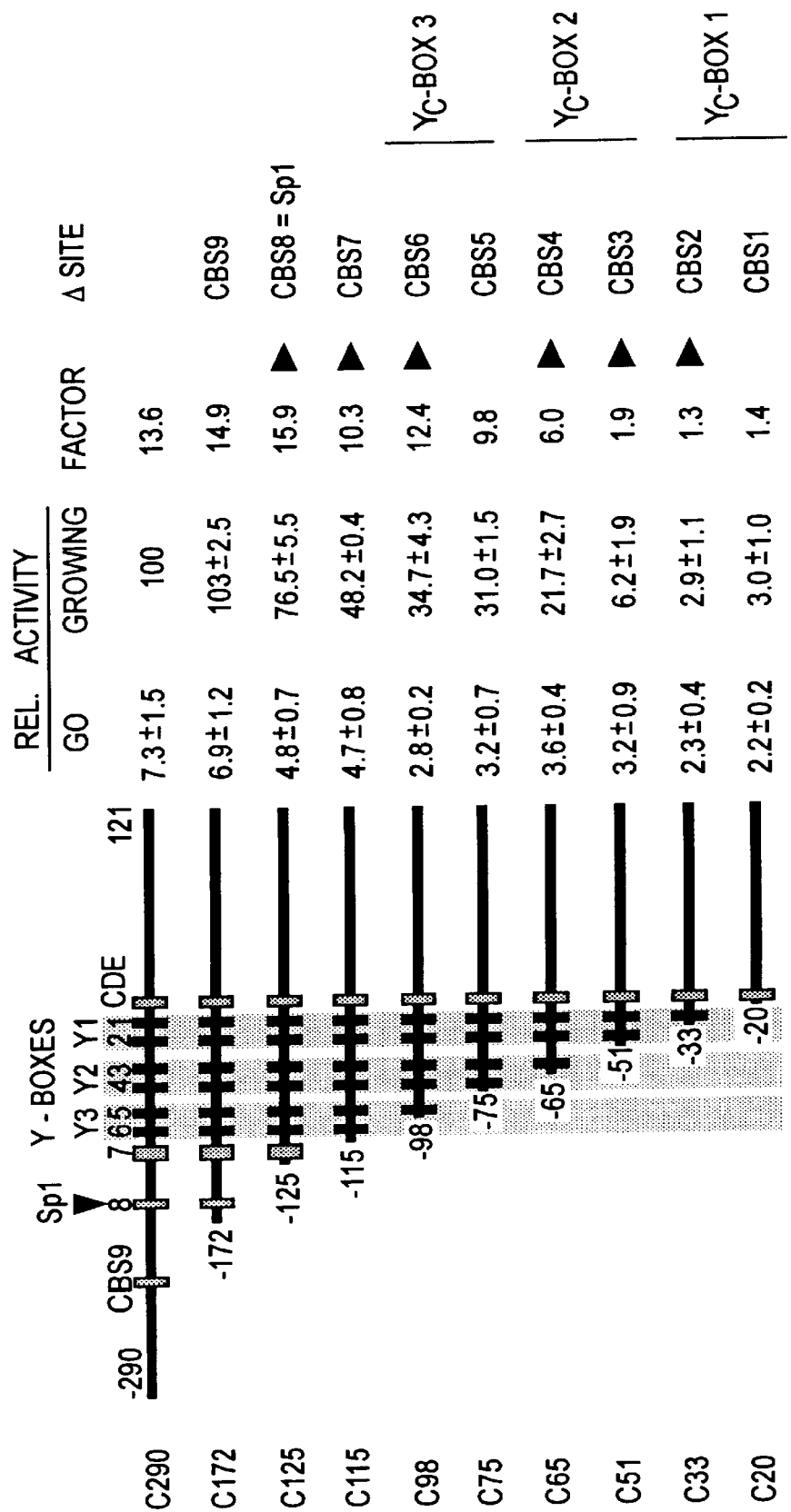
Figure 10:
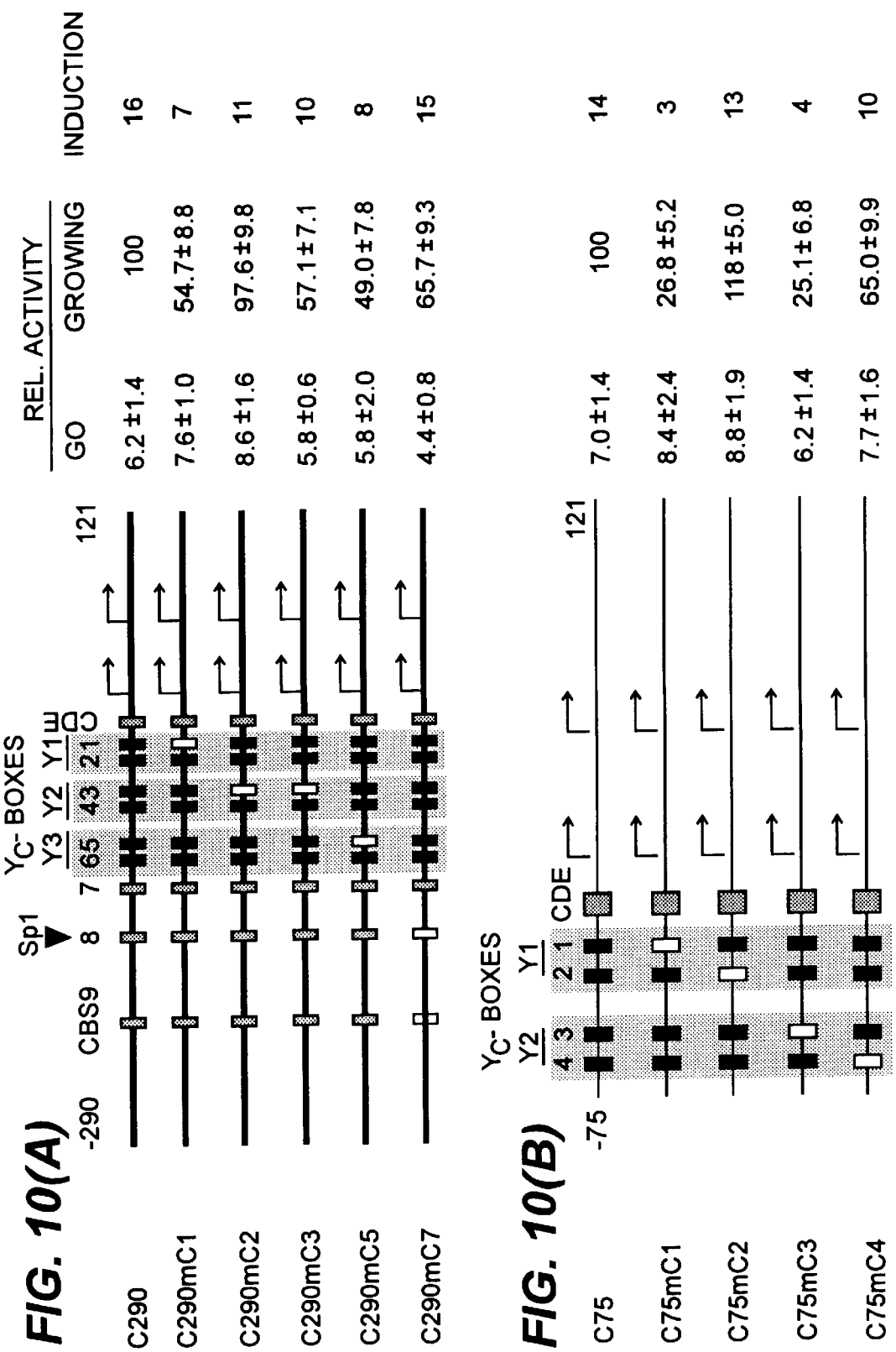
Figure 11:
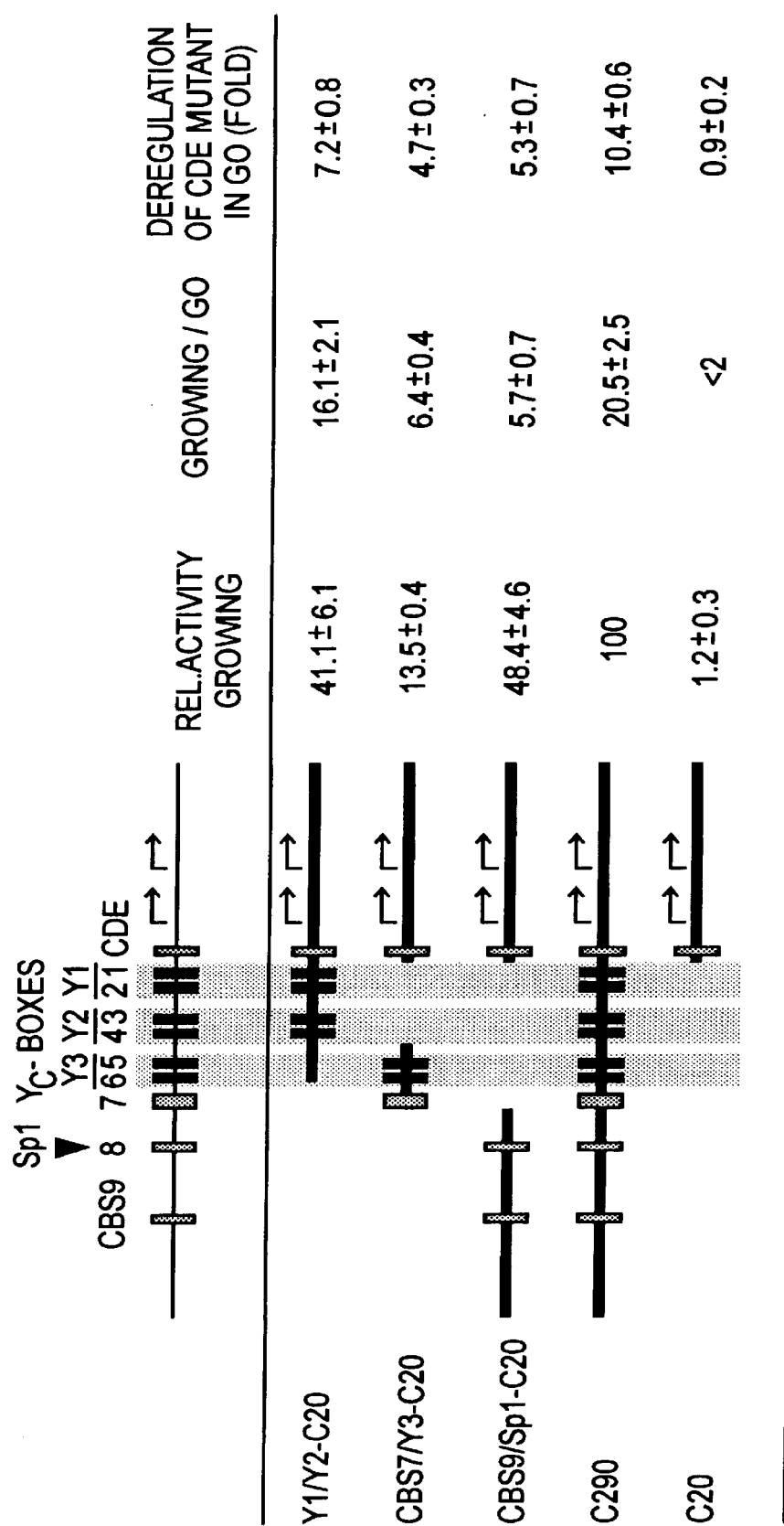

The data in FIG. 5B point to 2 additional regions in the promoter that seem to play a role in transcription. One is located far upstream (−835 to −1067) and its deletion leads to an increased activity, but the molecular basis underlying this effect is not clear. The other region is located at −74 to −169 and seems to contain a cell cycle-independent enhancer, since its deletion leads to a ~5-fold drop in activity in both $G_0$ and $G_2$ cells. The late S/$G_2$-specific transcription of the human cdc25C gene is therefore dependent on a DNA repressor element and the surrounding sequences. We have shown that the upstream sequences harbour multiple in vivo protein binding sites (FIG. 8) which interact with constitutive transcriptional activators (FIGS. 9–11). Major determinants in this enhancer region are a bona fide Sp1 site and three direct sequence repeats ($Y_c$-boxes; see FIG. 8B) each consisting of an element resembling a reverse CCAAT-box and an adjacent GC-rich motif. As indicated by genomic footprinting, functional analyses and in vitro protein binding studies (Barberis et al., 1987) and antibody supershifts (Mantovani et al., 1992) using nuclear extracts from HeLa cells (Dignam et al., 1983), the $Y_c$-boxes represent unusual binding sites for the CCAAT-box binding protein NF-Y/CBF (Dorn et al., 1987: van Hujisduifnen et al., 1990; Maity et al., 1983) and synergise in transcriptional activation.

Efficient transcription of the cdc25C promoter constructs was also seen in normally growing cells, even though only a relatively small fraction of the cell population is in G2 at any given time. We attribute this to the fact that the luciferase protein is relatively stable and could thus accumulate to high levels in the growing cells.

Identification of a Cell Cycle-regulated Protein Binding Site in vivo (CDE)

To analyse the mechanisms involved in cell cycle regulation of the cdc25C gene in detail we performed genomic dimethyl sulfate (DMS) footprint analysis of the region between nucleotides −80 and +15 using $G_0$ and stimulated ($G_2$) WI-38 cells, i.e. conditions of minimum and maximum expression of endogenous cdc25C (see FIGS. 1 and 4). FIG. 6A shows that within this region guanine residues in 4 distinct areas were protected from methylation by DMS. Protection of 3 sites was found to be constitutive, i.e. independent of the cell cycle. These sites, located at positions −28/−27,−39 and −58/−59 were termed constitutive binding sites 1, 2 and 3 (CBS 1, 2 and 3). Further footprint analysis of the region between nucleotides −310 and +65 has been made and a further 6 CBSs identified. See FIG. 8. Please note CBS 1 and 2, CBS 3 and 4, and CBS 5 and 6 are located within $Y_c$-boxes 1 to 3, respectively. The site identified by in vivo footprinting, located at positions −12 to −16, is of particular interest because protein binding to this sequence is cell cycle dependent (FIG. 5A). Thus, hardly any protection was seen in stimulated cells in $G_2$. whereas a clear protection was observed in both quiescent and normally cycling cells. This site was therefore termed cell cycle dependent element (CDE). The fact that no difference was seen among quiescent and growing cells is presumably due to the fact that the fraction of $G_2$ cells in normally cycling cells is relatively low (10–15%).

Figure 6B:
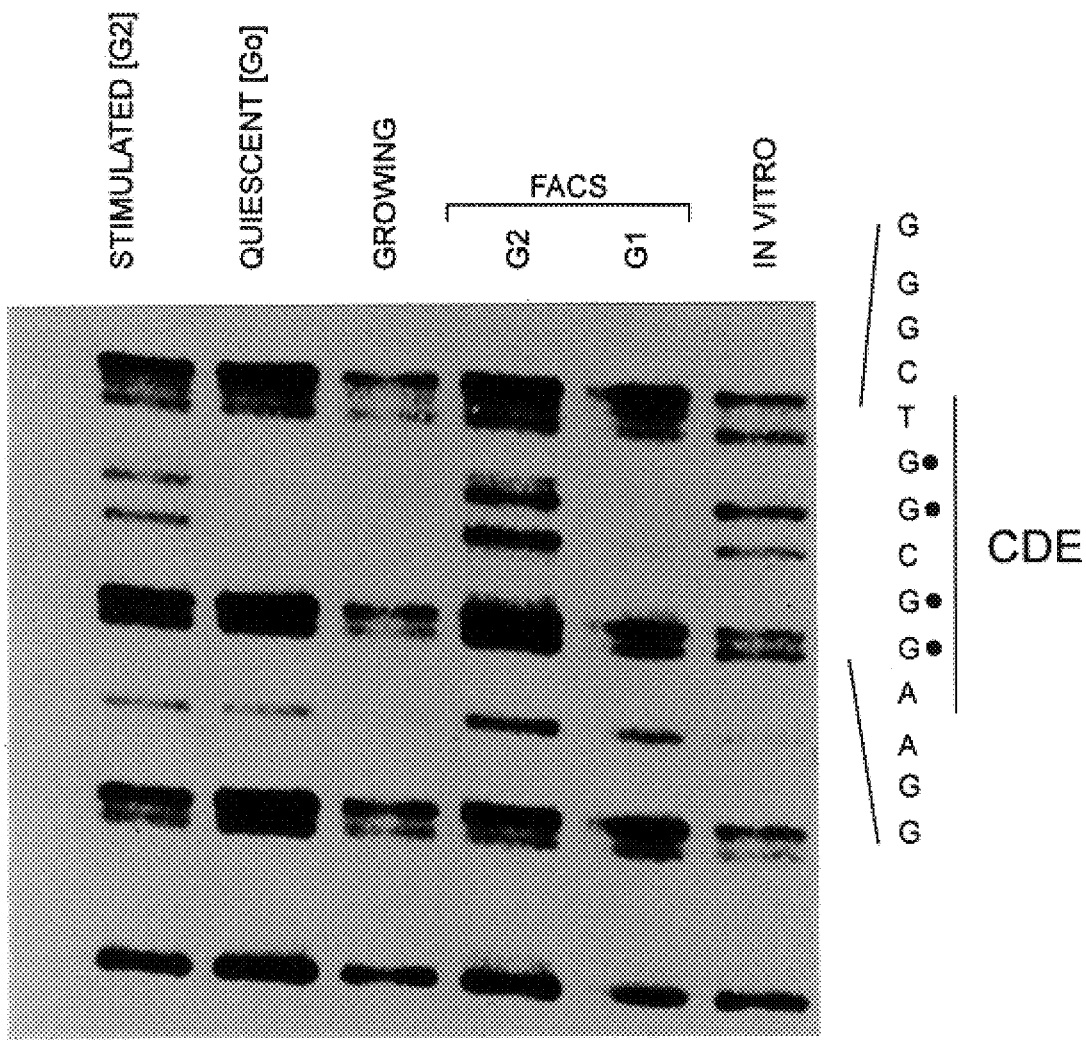

In order to rule out any artefacts arising from the synchronisation procedure, and to analyse whether the CDE footprint was also seen in $G_1$ cells rather than being $G_0$-specific, we repeated the experiment and this time included purified $G_1$ and $G_2$ cells obtained by preparative cell sorting of a normally cycling population of WI-38 cells using a fluorescence activating cell sorter (FACS). The results of this experiment are shown in FIG. 6B: four G residues within the CDE at positions −12, −13, −15 and −16 were protected in $G_1$ but not in $G_2$. We therefore conclude that protection of the CDE is seen in both $G_0$ and $G_1$ cells, indicating cell cycle regulated protein binding to the CDE.

The CDE is a Major Determinant of Cell Cycle Regulation of cdc25C Transcription in vivo In view of the cell cycle regulation seen with Δ74 (FIGS. 4B and 5), the results obtained by in vivo footprinting (FIGS. 6 and 8) and the transient expression analysis (FIGS. 2, 3 and 4), it can be seen that the CDE and the constitutive binding sites (CBS) 1 to 8 play a crucial role in cell cycle dependent activation of the cdc25C promoter. Since the CDE as a cell cycle regulated protein binding site was a particularly interesting candidate in this respect, we generated a C74-derived mutant with an altered CDE due to the exchange of 4 nucleotides, including 3 of the protected guanine residues. This construct (C74R1) and the parental (C74) plasmid were analysed in 4 independent transfection assays in $G_0$ versus stimulated ($G_2$) NIH3T3 cells, and in 2 assays comparing $G_0$ and normally growing cells. FIG. 7A shows graphic representations of two of these assays, all results are listed in FIG. 7B. The data clearly indicate that cell cycle regulation in C74R$_1$ was severely impaired. This loss of regulation was due to a dramatically increased activity in $G_0$ (average 12.8-fold; see FIG. 7B) while expression in $G_2$ was hardly affected (average 1.6-fold). Taken together with the protein binding studies, this result strongly suggests that the CDE binds a protein or a protein complex that acts as a repressor in $G_0/G_1$ and is released in the $G_2$ phase of the cell cycle.

In summary the functional analysis in transient luciferase assays of various truncated cdc25C promoter constructs showed that just 74 bp of upstream sequence plus 121 bp of transcribed non-translated sequence were sufficient to confer cell cycle regulation, i.e. induction of the reporter gene around late S/$G_2$. Experiments currently in progress indicate that a 3' truncation removing an additional 51 nucleotides has no influence on the function of the promoter fragment, suggesting that cell cycle-dependent transcription requires no more than 74 bases of upstream sequence plus a 50-nucleotide stretch containing the 2 initiation sites.

Genomic DMS footprinting revealed the presence of a protein binding site that is occupied in a cell cycle dependent fashion directly adjacent 5' to the first initiation site. This element, termed CDE, contains 4 G residues in the coding strand at −12, −13, −15 and −16 that are protected specifically in $G_0$, but not in $G_2$. The validity of this observation is greatly enhanced by the fact that a $G_1$-specific protection pattern was also seen with sorted cells of a normally cycling population. Since these cells were not synchronised by any means and were fixed following in vivo exposure to DMS prior to the sorting procedure, we can largely rule out any experimental artefacts. We therefore conclude that the observed cell cycle-regulated protein binding to the CDE reflects the physiological situation very closely.

The pattern of protein binding to the CDE raised the possibility that this element mediates cell cycle regulation through the interaction with a repressor in $G_0/G_1$. This hypothesis could be confirmed by functional assays which showed that mutations in the CDE led to a dramatic increase in reporter gene expression in $G_0/G_1$, thus largely abolishing cell cycle regulation of the luciferase reporter construct. These results establish the CDE as a cell cycle-regulated repressor binding site playing a major role in the cell cycle-controlled transcription of the cdc25C gene. The very poor transcription seen with C20 strongly suggest that the CDE acts solely as a repressor element and is not endowed with any significant enhancer function that could be under cell cycle control. This distinguishes the CDE-binding activity from the transcription factors of the E2F/DP family which are repressed in $G_1$ through their interaction with the retinoblastoma suppressor protein pRB but act as transcriptional activators later in the cell cycle (for reviews see Nevins 1992; La Thangue 1994).

Figure 12:
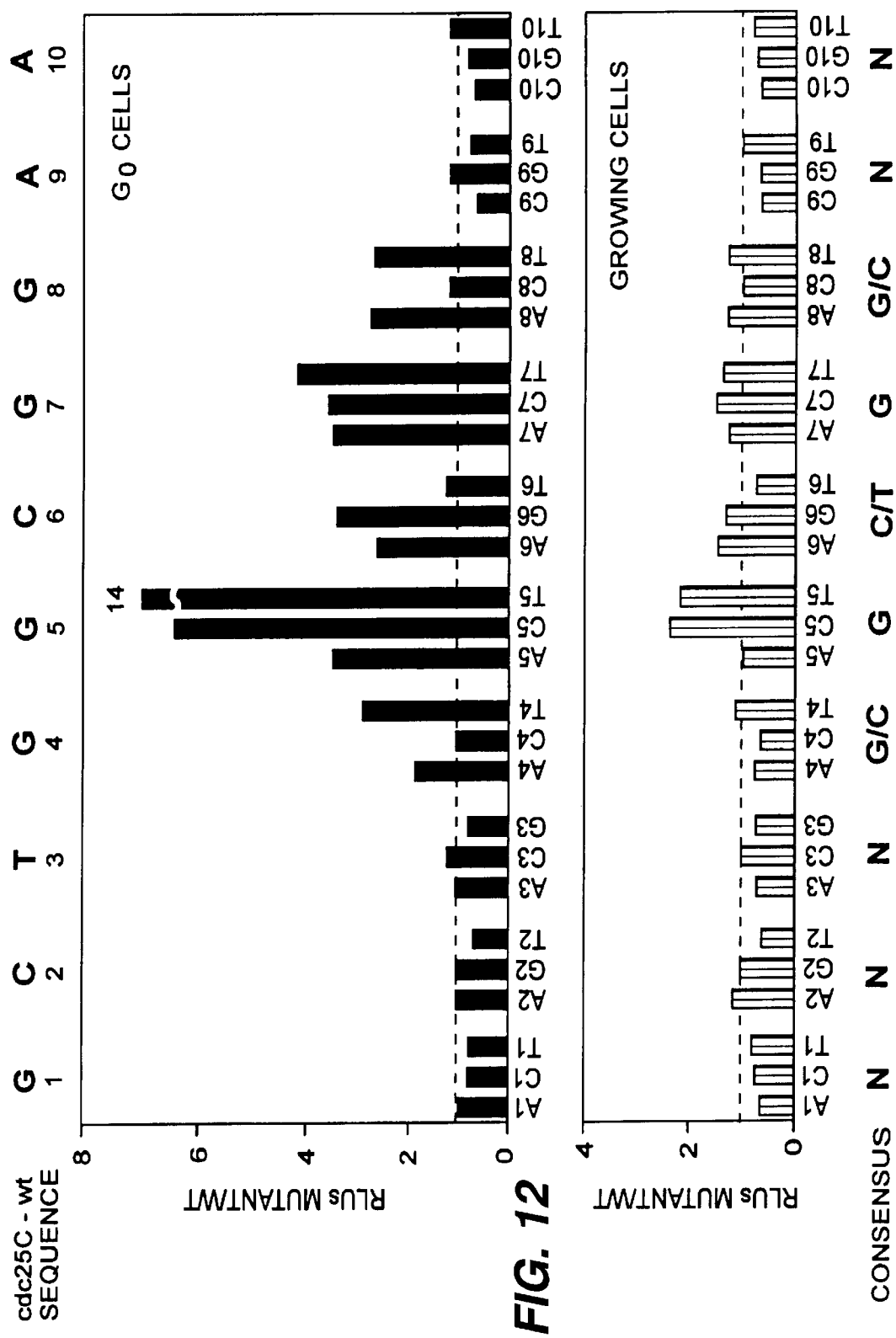
Figure 13:
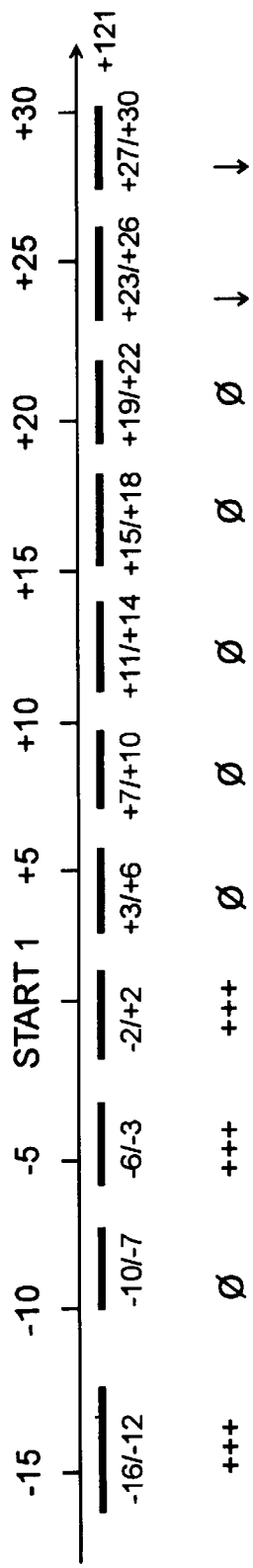
Figure 14:
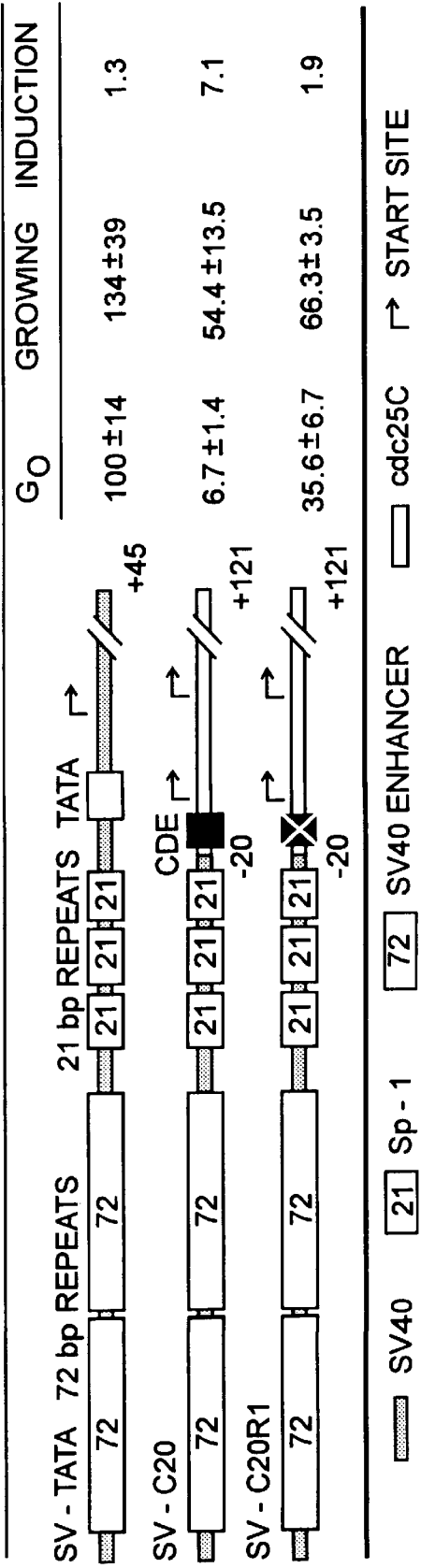

Further mutagenesis of the CDE (FIG. 12) and the region downstream to position +30 (FIG. 13) defined the precise position of the CDE to nucleotides −17 to −12 and revealed two additional elements that are crucial for the proper functioning of the CDE and thus for cell cycle regulation of the cdc25C promoter. Changes in the sequences either around nucleotide positions −6 to −3 the cell cycle homology region (CHR), discussed below, or overlapping the first major initiator Inr at nucleotide positions −2 to +2 led to the same deregulation as mutation of the CDE itself. As shown by in vitro protein binding studies (Barberis et al., 1987) using HeLa cell nuclear extract (Dignam et al., 1983), both elements interact with different proteins. The Inr itself interacting with a YY1 complex (Seto et al., 1991), as shown by supershifts and the binding of recombinant YY1 protein. These results strongly suggest that the function of the CDE-binding protein is dependent on additional interactions with at least one other protein binding to the CHR and perhaps the Inr regions and that the CDE-CHR elements have to be contiguous with an Inr. The implication of this finding for the construction of chimaeric promoters is that the promoter of the cdc25C gene or other cell cycle regulated promoters must contain the CDE, CHR and the Inr and must be fused to a heterologous enhancer in order to confer cell cycle regulation on the enhancer. Based on this and using standard molecular biological techniques, a cdc25C promoter fragment (−20 to +121) was fused to the SV40 early promoter/enhancer region. The chimaeric promoter obtained exhibited the same cell cycle regulation as the wild type cdc25C gene. See FIG. 14. It would be obvious to one skilled in the art that instead of the SV40 enhancer tissue-specific enhancers could be used (Sikora, 1993), which in conjunction with a CDE-CHR-Inr unit would yield chimeric transcription control elements that are both cell cycle-regulated and tissue/cell type-specific.

Alignment of the cdc25C CDE-CHR region with the sequences of other known cell cycle regulated promoters revealed striking similarities in the case of cyclin A, cyclin F (Kraus et al., 1994), cdc2 (Dalton, 1992) and β-myb (Lam et al., 1995). Both CDE- and CHR-like elements were found in these promoters at similar locations relative to the transcription start sites, see FIG. 15. Significantly, any base changes seen in the CDEs in these promoters were found to be tolerated with respect to cell cycle regulation when introduced into the cdc25C CDE. Results not shown. In view of these observations we performed genomic footprinting with the cyclin A and cdc2 promoters and found the same situation as in the case of cdc25C, i.e., the $G_0/G_1$-specific binding of a protein/protein complex to the CDE. Results not shown. In addition, point mutations largely abrogated cell cycle regulation, confirming the functional significance of the CDE-CHR region in these promoters. These observations also indicate that the CDE-CHR elements are not totally Inr-specific, since the cyclin A, cdc2 and B-myb promoters do not show obvious homologies with the Inr of the cdc25C gene, but rather dependent on a short distance between them and an Inr.

Figure 16:
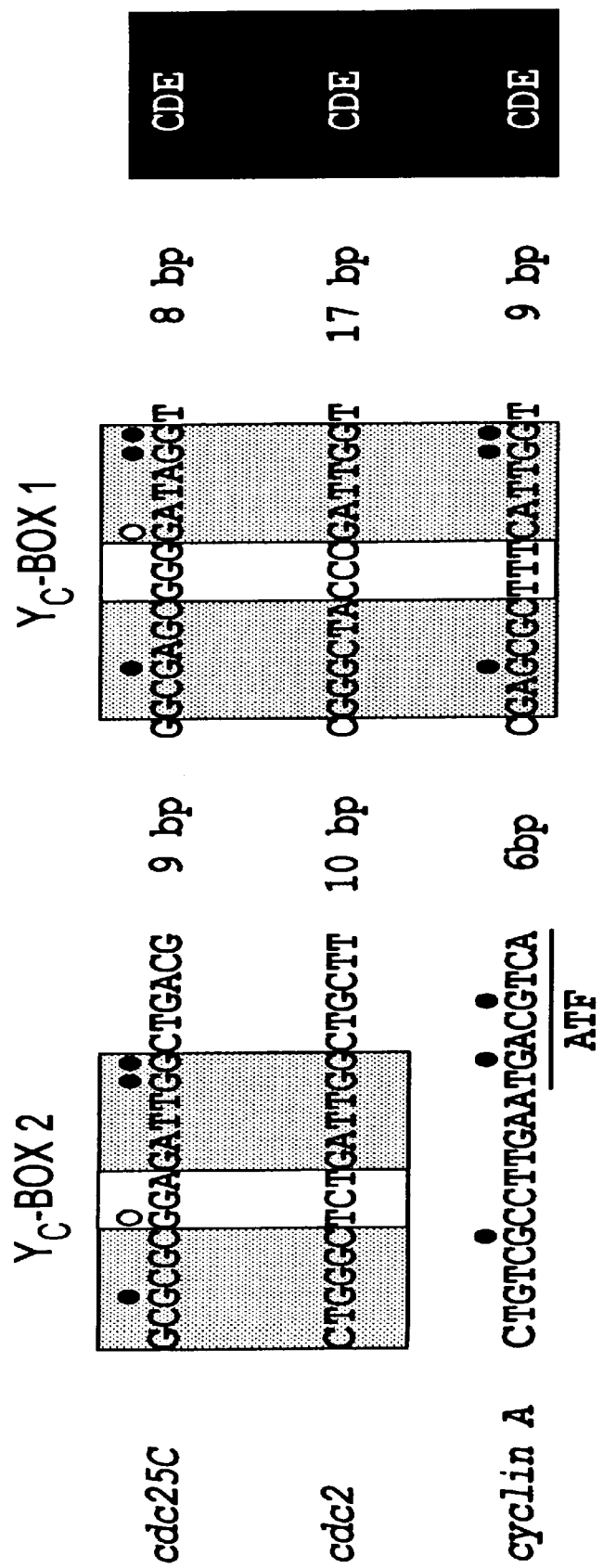

Alignment of the sequences upstream of the CDE also revealed striking similarities in the region of $Y_c$-boxes 1 and 2 (FIG. 16), pointing to common targets of repression. Taken together, these data clearly suggest that CDE-mediated repression is a frequent mechanism of cell cycle regulated transcription, and that the targets of this negative regulatory mechanism are often the glutamine-rich CCAAT-box binding proteins (such as NF-1/CTF) and Sp1 family members interacting with the respective enhancers.

The mechanism leading to $G_0/G_1$ specific repression has been shown to be mediated by a DNA repressor element which is believed to interfere with the function of the activators interacting with upstream located enhancer elements. In the cdc25C gene the sequences upstream of the CDE contain a Sp1 site and 3 $Y_c$-boxes which act as cis acting transcriptional activators (FIGS. 5 and 9 to 11). The CDF binding protein/protein complex, E-CHR is believed to interfere with the function of constitutive, glutamine-rich activators thereby repressing transcription of the cdc25C gene.

Our observations suggest DNA repressor elements may mediate interference with constitutive glutamine-rich activators thereby providing the basis of the periodicity of transcription.

The implication of this finding for the construction of chimaeric tissue-specific/cell type-specific, cell cycle regulated promoters is that tissue-specific enhancers interacting with e.g. glutamine-rich activators are particularly suitable elements to be fused with the DNA repressor element containing cdc25C promoter and other cell cycle regulated promoters operably linked to a DNA repressor element.

References

Abken, H. and Reifenrath, B. (1992) *Nucl. Acids Res.*, 20, 3527.
Barberis, A., Superti-Furga, G. and Busslinger, M. (1987) *Cell*, 50, 347–359.
Briggs, M. R., Kadonaga, J. T., Bell, S. P. and Tijian, R. (1986) *Science*, 234, 47–52.
Cowell, I. G. (1994) *TIBS*, 19, 38–42.
Dalton, S. (1992) *EMBO J.* 11, 1797–1804
Dignam, J. D., Lebovitz, R. M. and Roeder, R. G. (1983) *Nucl. Acids. Res.*, 11, 1475–1489.
Dihaio, et al., *Surgery*, 116, 205 (1994)
Dorn, A., Bollekens, J., Staub, A., Benoist, C. and Mathis, D. (1987) *Cell*, 50, 863–872.
Ducommun, B., Draetta, G., Young, P. and Beach, D. (1990) *Biochem. Bioshys. Res. Commun.*, 167, 301–309.
Dunphy, W. G. and Kumagai, A. (1991) *Cell*, 67, 189–196.
Edgar, B. A. and O'Farrell, P. H. (1989) *Cell*, 57, 177–187.
Galaktionov, K. and Beach, D. (1991) *Cell*, 67, 1181–1194.
Gautier, J., Solomon, M. J., Booher, R. N., Bazan, J. F. and Herber, B., Truss, M., Beato, M. and Müller, R. (1994) *Oncogene*, 9, 1295–1304.
Harris, et al., *Gene Therapy*, 1, 170, (1994)
Hisatake, K., Hasegawa, S., Takada, R., Nakatani, Y., Horikoshi, M. and Roeder, R. G. (1993) *Nature*, 362, 179–181.
Jessus, C. and Beach, D. (1992) *Cell*, 68, 323–332.
Kirschner, M. W. (1991) *Cell*, 67, 197–211.
Kraus, B. et al. (1994) *Genomics*, 24, 27–33.
Kumagai, A. and Dunphy, W. G. (1991) *Cell*, 64, 903–914.
La Thangue, N. B. (1994) *Curr. Opin. Cell Biol.*, 6, 443–450.
Larn, E. W. -F and R. J. Watson (1993) *EMBO J.* 12, 2705–2713.
Maity, S. N., Sinha, S., Ruteshouser, E. C. and de Crombrugghe, B. (1993) *J. Biol. Chem.* 267, 16574–16580.
Mantovani, R., Pessara, U., Tronche, F., Li, X. Y., Knapp, A. M., Pasquali, J. L., Benoist, C., and Mathis, D. (1992) *EMBO J.*, 11, 3315–22.
Meyer, R., Hatada, E. N., Hohmann, H. -P., Haiker, M., Bartsch, C., Rothlisberg, U., Lahm, H. -W., Schlaeger, E. J., van Loon, A. P. G. M. and Scheidereit, C. (1991) *Proc. Natl. Acad. Sci. USA*, 88, 966–970.
Millar, J. B. A., Blevitt, J., Gerace, L., Sadhu, K., Featherstone, C. and Russell, P. (1991) *Proc. Natl. Acad. Sci. USA*, 88, 10500–10504.
Millar, J. B. A., McGowan, C. H., Lenaers, G., Jones, R. and Ruppert, S., Wang, E. H. and Tijian, R. (1993) *Nature*, 362, 175–179.
Millar, J. B. A. and Russell, P. (1992) *Cell*, 68, 407–410.
Mullen, *Pharmac. Ther.* 63, 199 (1994)
Moreno, S., Nurse, P. and Russell, P. (1990) *Nature*, 344, 549–552.
Nevins, J. R. (1992) *Science*, 258, 424–429.
Osaki, et al., *Cancer Res.*, 54, 5258, (1994).
Pfeifer, G. P., Steigerwald, S., Mueller, P. R. and Riggs, A. D. (1989) *Science*, 246, 810–813.
Russell, P. and Nurse, P. (1986) *Cell*, 45, 145–153.
Russell, P. (1991) *EMBO J.*, 10, 4301–4309.
Sadhu, K., Reed, S. I., Richardson, H. and Russell, P. (1990) *Proc. Natl. Acad. Sci. USA*, 87, 5139–5143.
Saiki, R. K., Gelfand, D. H., Stoffel, S., Scharf, S. J., Higuchi, R., Horn, G. T., Mullis, K. B. and Erlich, H. A. (1988) *Science*, 239, 487–491.
Seto, E., Shi, Y. and Shenk, T. (1991) *Nature* 354, 241–245
Sikora, K (1993) *Trends Biotech*, 11, 197–201.
Sikora, et al., *Ann. N.Y. Acad. of Sciences*, 716, 115 (1994)
Singh, H., LeBowitz, J. H., Baldwin Jr., A. S. and Sharp, P. A. (1988) *Cell*, 52, 415–423.
Strausfeld, U., Labbé, J. C., Fesquet, D., Cavadore, J. C., Picard, A., Sadhu, K., Russel, P. and Dorée, M. (1991) *Nature*, 351, 242–245.
van Hujisduifnen, H. R, Li, X. Y., Black, D., Matthes, H., Benoist, C. and Mathis, D. (1990) *EMBO J*, 9, 3119–3127.
Wang, E. H. and Tijian, R. (1994) *Science*, 263, 811–814.
Woods, D. B., Ghysdael, J. and Owen, M. J. (1992) *Nucleic Acids Research*, 20, 699–704.

All the above references are herein incorporated by reference.

What is claimed is:

1. A vector for the expression of a desired gene product in a cell, comprising a structural gene encoding the desired gene product operably linked to a chimeric promoter, the promoter comprising a DNA repressor element comprising a sequence selected from the group consisting of the sequences TGGCGG, GCGCGG, TCGCGG and GCCGGG, which interacts with a cell cycle specific repressor, a cell cycle homology region comprising a sequence selected from the group consisting of the sequences GTTTGAA and ACTTGAA, a transcription initiation site and enhancer elements, in order to regulate gene expression in a cell cycle specific mamner, wherein the promoter and the repressor element are not naturally present together.

2. A vector according to claim 1, wherein the promoter is further controlled by a tissue- or cell type-specific regulatory element.

3. A vector according to claim 1, wherein the DNA repressor element comprises at least part of the sequence 5'-GCTGGCGGAAGGTTTGAATGG-3' (SEQ ID NO:1) or a mutant or homologue of SEQ ID NO:1, wherein the DNA repressor element is functional to bind the cell specific repressor and wherein the DNA repressor reacts with a cell specific repressor to regulate gene expression in a cell cycle specific manner.

4. A vector according to claim 1, wherein the transcription initiation site is the first major transcription initiation site of a cdc25C gene.

5. A vector according to claim 1, wherein the DNA repressor element is from a cell cycle regulated gene.

6. A vector according to claim 1, wherein the DNA repressor element is from a cdc25C gene, a cdc2 gene or a cyclin A gene.

7. A vector according to claim 1 wherein the gene product is a cytotoxic or cytostatic agent or a prodrug activating enzyme.

8. A vector according to claim 2, wherein the tissue- or cell type-specific regulatory element is an enhancer.

9. A vector according to claim 2 or claim 8, wherein the regulatory element is an enhancer which is activated by glutamine-rich activators.

* * * * *